US012629022B2

(12) United States Patent
Davis, III et al.

(10) Patent No.: US 12,629,022 B2
(45) Date of Patent: May 19, 2026

(54) PRISMATIC LENS FOR REDUCING A DYNAMIC ALIGNMENT DIFFERENTIAL

(71) Applicant: Newton, Inc., Coppell, TX (US)

(72) Inventors: John Merrill Davis, III, Midlothian, VA (US); Jeffrey P. Krall, Mitchell, SD (US)

(73) Assignee: Newton, Inc., Coppell, TX (US)

( * ) Notice: Subject to any disclaimer, the term of this patent is extended or adjusted under 35 U.S.C. 154(b) by 255 days.

(21) Appl. No.: 18/295,405

(22) Filed: Apr. 4, 2023

(65) Prior Publication Data

US 2024/0335109 A1     Oct. 10, 2024

(51) Int. Cl.
   *A61B 3/02*     (2006.01)
   *A61B 3/10*     (2006.01)
   *A61B 3/113*    (2006.01)
   *A61B 3/12*     (2006.01)
   *G02C 7/14*     (2006.01)

(52) U.S. Cl.
   CPC ................ *A61B 3/113* (2013.01); *G02C 7/14* (2013.01)

(58) Field of Classification Search
   CPC ......... A61B 3/02; A61B 3/102; A61B 3/1025; A61B 3/113; A61B 3/1015; A61B 3/1225; A61B 3/024; A61B 3/005
   USPC ....... 351/200, 205, 206, 209, 210, 221–223, 351/245–246
   See application file for complete search history.

(56) References Cited

U.S. PATENT DOCUMENTS

| | | |
|---|---|---|
| 2013/0278899 A1 | 10/2013 | Waldorf et al. |
| 2018/0004010 A1 | 1/2018 | Kaga et al. |
| 2018/0028057 A1 | 2/2018 | Oz et al. |
| 2018/0239423 A1 | 8/2018 | Mardanbegi et al. |
| 2019/0029511 A1* | 1/2019 | van Dijk ................. A61B 3/111 |
| 2019/0046029 A1* | 2/2019 | Tomasi .................... A61B 3/00 |
| 2019/0209005 A1 | 7/2019 | Barraza-Bernal et al. |
| 2022/0047158 A1 | 2/2022 | Ghajar et al. |

* cited by examiner

*Primary Examiner* — Dawayne Pinkney

(57) ABSTRACT

A method for determining a binocular dynamic alignment can include the following steps: causing a patient to gaze at a starting target with a left eye and a right eye, with a display; shifting the target in a first direction by a first target shift angle at a first target shift time, with the display; measuring a first dynamic alignment differential between the left eye and the right eye acquiring the first-shifted target, with an eye tracker; shifting the first-shifted target in a second direction at a second target shift time, with the display; measuring a second dynamic alignment differential between the left eye and the right eye acquiring the second-shifted target with the eye tracker; determining an average dynamic alignment differential from the first dynamic alignment differential and the second alignment differential, with a computer; and determining a prescription prism to reduce the average dynamic alignment differential.

21 Claims, 19 Drawing Sheets method for determining
a binocular dynamic
alignment 100

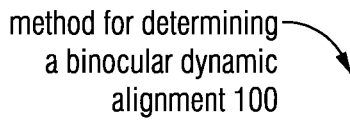

110 — causing a patient to gaze at a starting target with a left eye and a right eye, with a display 120 — shifting the target in a first direction by a first target shift angle at a first target shift time, with the display 130 — measuring a first dynamic alignment differential between the left eye and the right eye acquiring the first-shifted target, with an eye tracker 140 — shifting the first-shifted target in a second direction by a second target shift angle at a second target shift time, with the display 150 — measuring a second dynamic alignment differential between the left eye and the right eye acquiring the second-shifted target with the eye tracker 160 — determining an average dynamic alignment differential from the first dynamic alignment differential and the second alignment differential, with a computer 170 — determining a prescription prism to reduce the average dynamic alignment differential

FIG. 3A

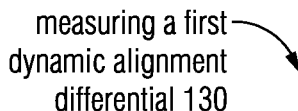

measuring a first
dynamic alignment
differential 130

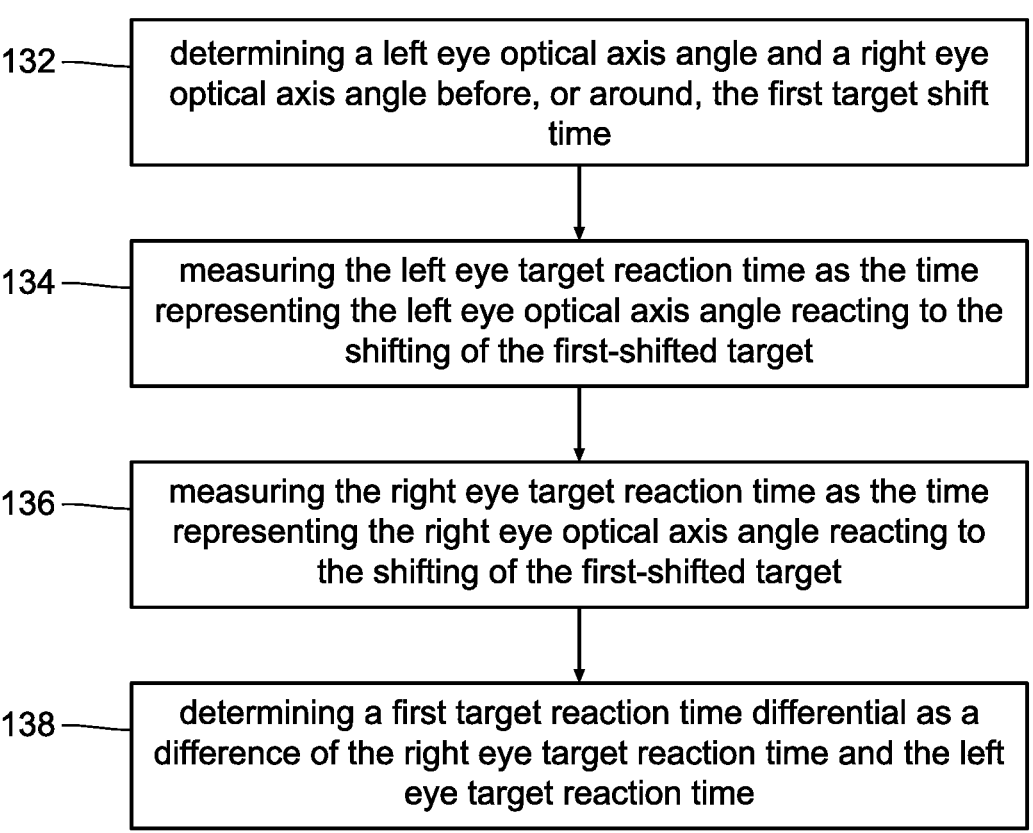

132 — determining a left eye optical axis angle and a right eye optical axis angle before, or around, the first target shift time 134 — measuring the left eye target reaction time as the time representing the left eye optical axis angle reacting to the shifting of the first-shifted target 136 — measuring the right eye target reaction time as the time representing the right eye optical axis angle reacting to the shifting of the first-shifted target 138 — determining a first target reaction time differential as a difference of the right eye target reaction time and the left eye target reaction time

Figures 4A, 4B:
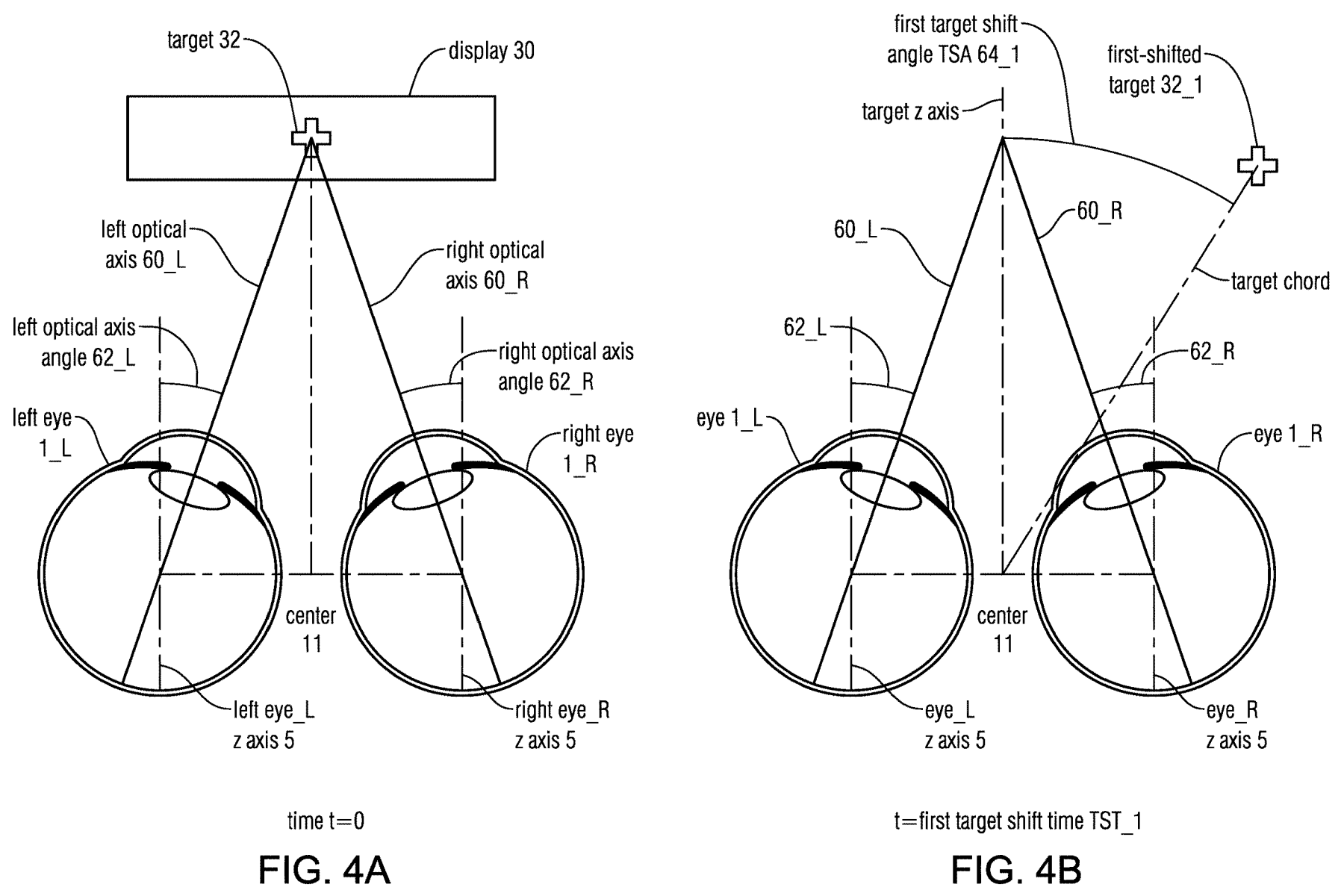

FIG. 3B first-shifted target 32_1
target chord
eye 1_R
62_R
eye_R
z axis 5
first target shift angle TSA 64_1
60_R
target z axis
center 11
60_L
eye_L
z axis 5
62_L
eye 1_L t=first target shift time TST_1

FIG. 4B display 30
right optical axis 60_R
right optical axis angle 62_R
right eye 1_R
right eye R
z axis 5
target 32
center 11
left optical axis 60_L
left optical axis angle 62_L
left eye L
z axis 5
left eye 1_L time t=0

FIG. 4A t = left-eye target reaction time TRT_L t = right-eye target reaction time TRT_R t=left-eye target acquisition time TAT_L t=right-eye target acquisition time TAT_R

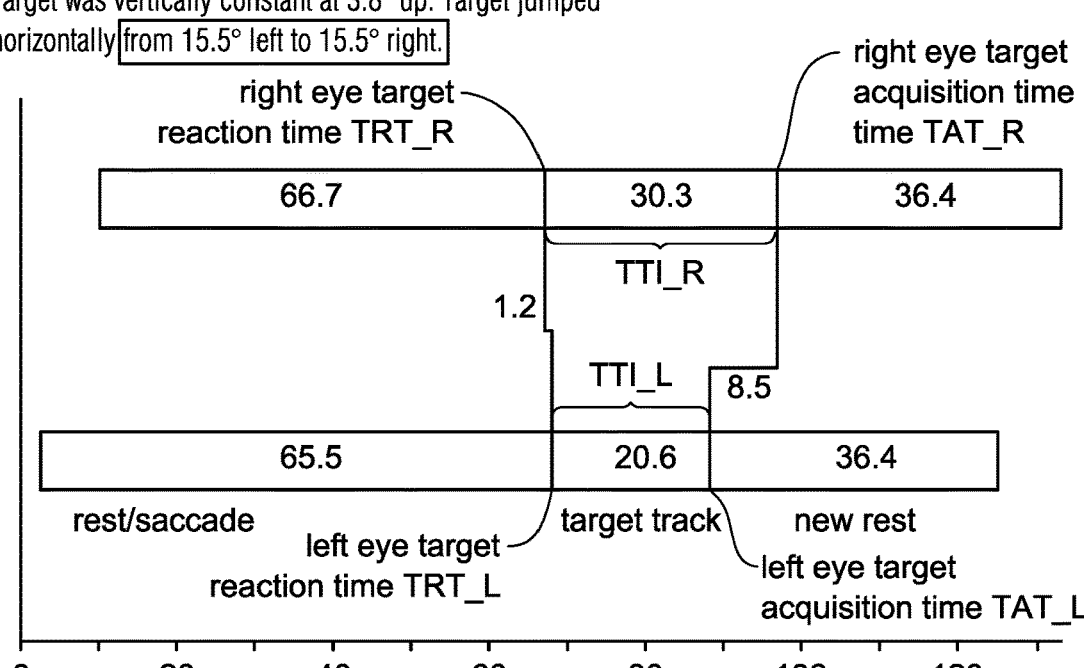
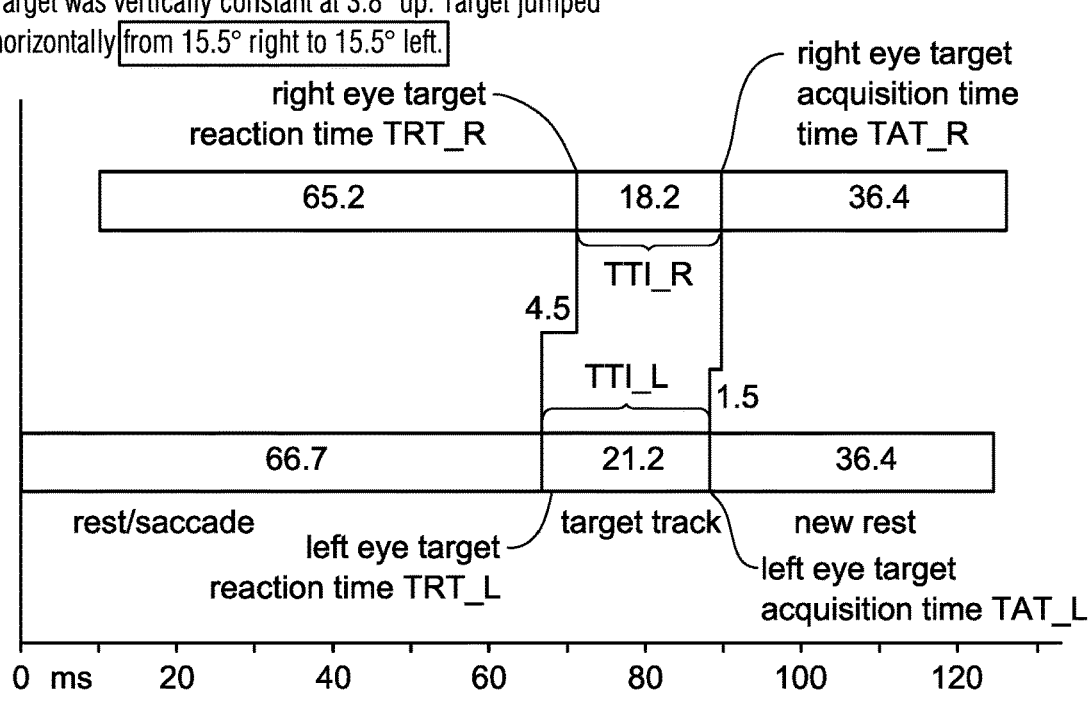
FIG. 8A

Summary 1: Relative to display center:
Target was vertically constant at 3.8° up. Target jumped
horizontally from 11.7° left to 11.7° right.
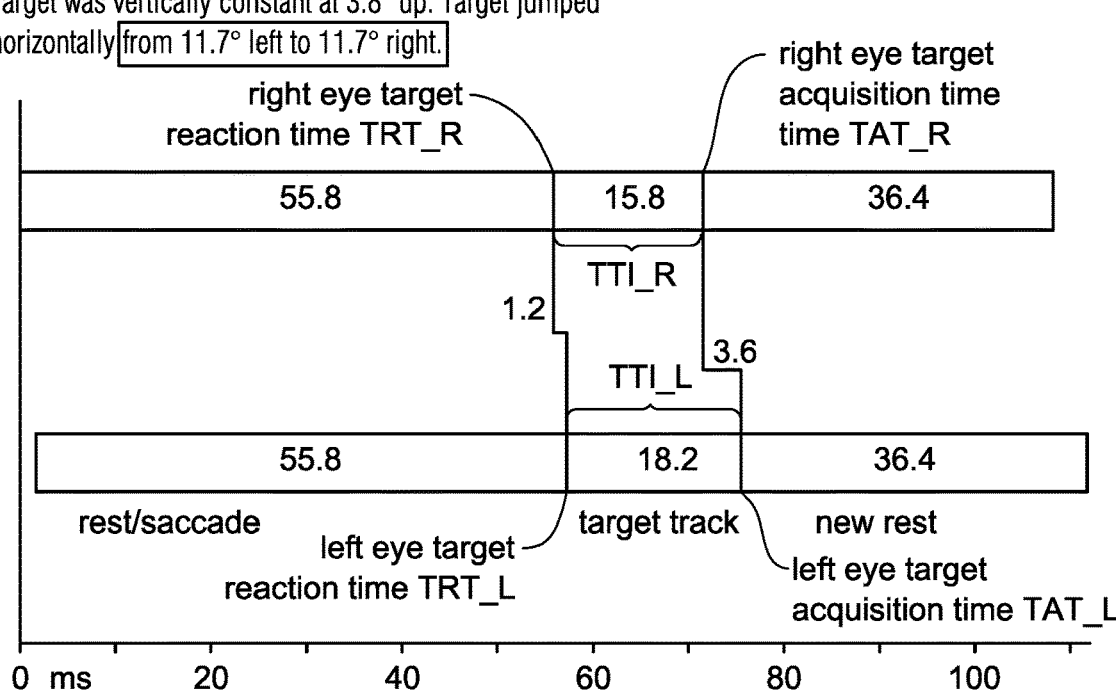
Summary 1: Relative to display center:
Target was vertically constant at 3.8° up. Target jumped
horizontally from 11.7° right to 11.7° left.
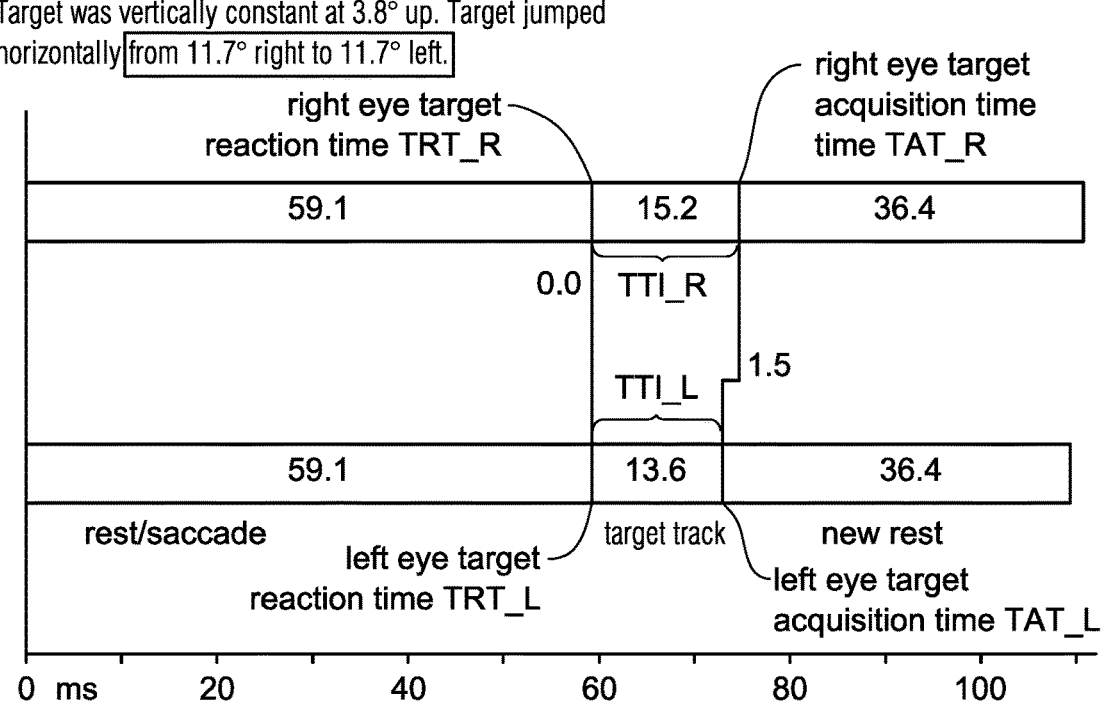
FIG. 8B method for determining
a binocular dynamic
alignment 200

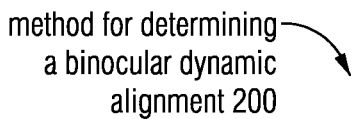

210 ── causing a patient to gaze at a starting target with a left
eye and a right eye, with a display 220 ── dynamically varying a characteristic of the target, with the
display 230 ── measuring a left-eye dynamic characteristic of the left eye
tracking the varying target and a right-eye dynamic
characteristic of the right eye tracking the target, with an
eye tracker 240 ── determining an average dynamic alignment differential
between the left-eye dynamic characteristic and the
right-eye dynamic characteristic over the tracking the
varying target, with a computer 250 ── determining a prescription prism to reduce the average
dynamic alignment differential

FIG. 11

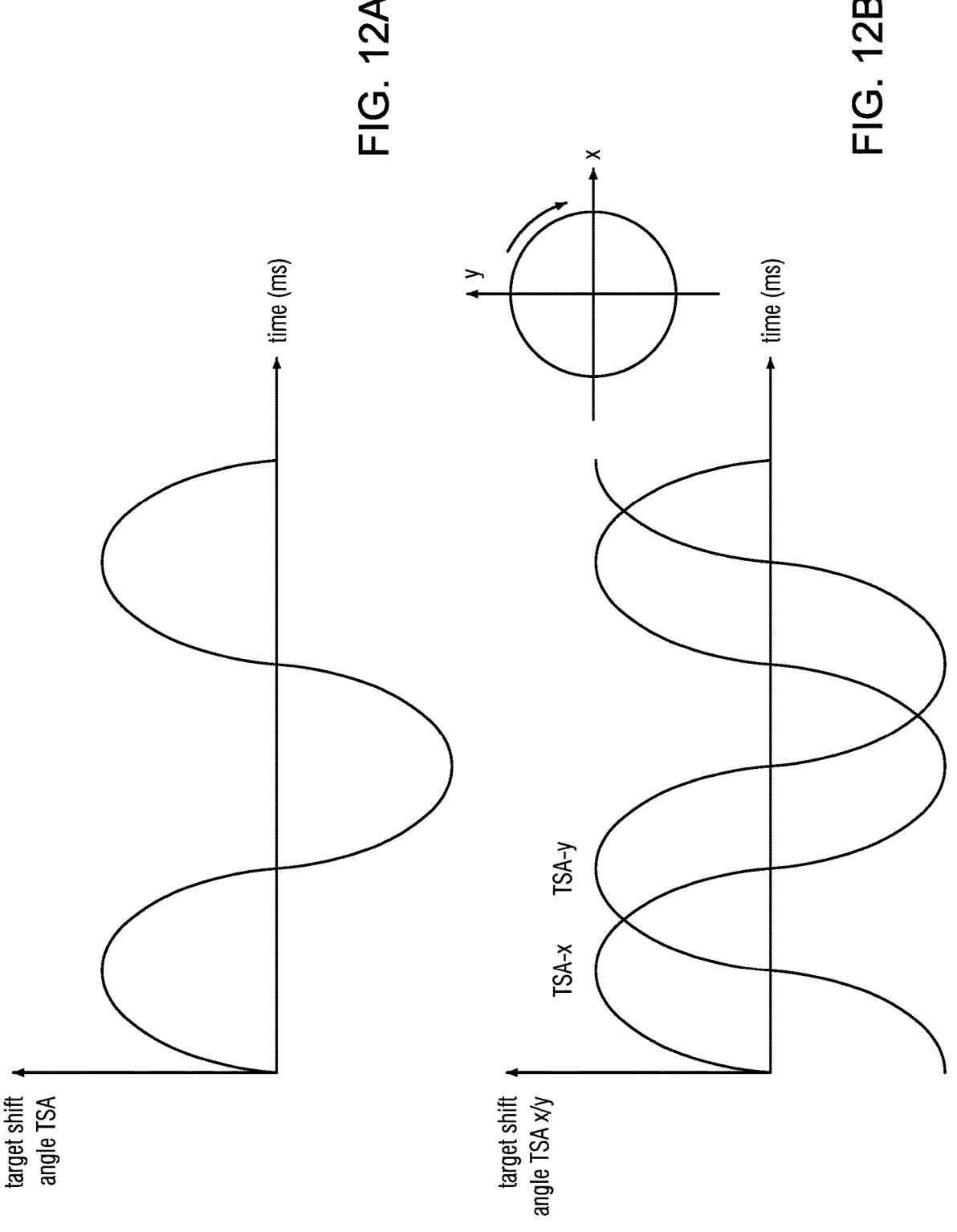

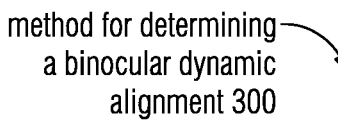

method for determining
a binocular dynamic
alignment 300

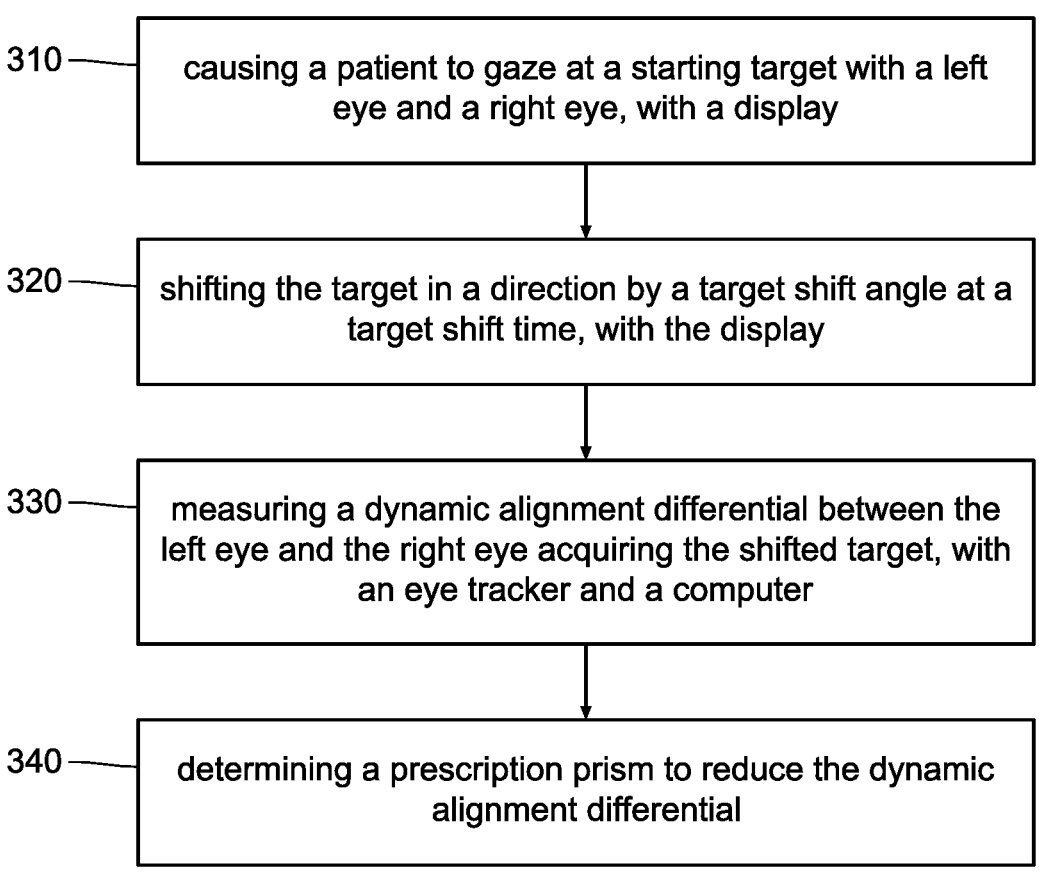

310 — causing a patient to gaze at a starting target with a left eye and a right eye, with a display 320 — shifting the target in a direction by a target shift angle at a target shift time, with the display 330 — measuring a dynamic alignment differential between the left eye and the right eye acquiring the shifted target, with an eye tracker and a computer 340 — determining a prescription prism to reduce the dynamic alignment differential

FIG. 13

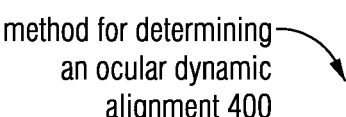

method for determining an ocular dynamic alignment 400

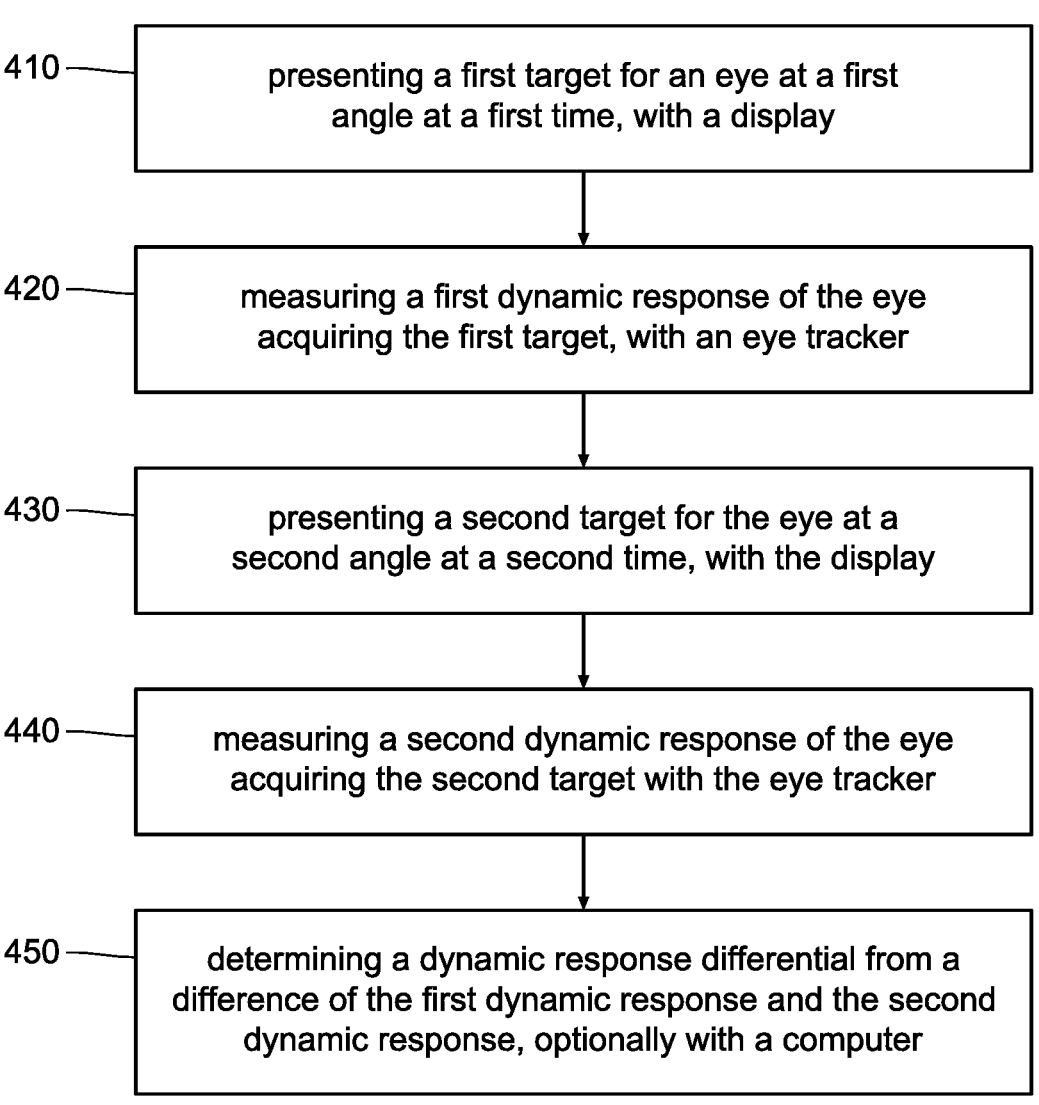

410 — presenting a first target for an eye at a first angle at a first time, with a display 420 — measuring a first dynamic response of the eye acquiring the first target, with an eye tracker 430 — presenting a second target for the eye at a second angle at a second time, with the display 440 — measuring a second dynamic response of the eye acquiring the second target with the eye tracker 450 — determining a dynamic response differential from a difference of the first dynamic response and the second dynamic response, optionally with a computer

FIG. 15

PRISMATIC LENS FOR REDUCING A DYNAMIC ALIGNMENT DIFFERENTIAL

BACKGROUND

The misalignment, or alignment differential between the eyes can cause serious medical symptoms, including headaches and migraines. Several of these can be cured by performing diagnostic measurements that were developed for identifying static misalignments, and by prescribing corresponding eyeglasses with a prism or a contour prism. The known symptoms of statically misaligned eyes include many types of headaches, dry eyes, neck tension, and asthenopia. These symptoms can escalate to nausea and/or dizziness and are implicated as a source of migraine headaches. However, a significant fraction of patients who manifest these symptoms either 1) show no significant static misalignment or 2) obtain best relief with a prism prescription different from that indicated by the measurement of their static misalignment. Therefore, there is a need for uncovering and identifying additional modes of eye misalignment and creating repeatable and reliable means of detecting and quantifying these modes for the purposes of medical research and medical practice.

SUMMARY

To address the above listed needs, a method for determining a binocular dynamic alignment can include the following steps: causing a patient to gaze at a starting target with a left eye and a right eye, with a display; shifting the target in a first direction by a first target shift angle at a first target shift time, with the display; measuring a first dynamic alignment differential between the left eye and the right eye acquiring the first-shifted target, with an eye tracker; shifting the first-shifted target in a second direction at a second target shift time, with the display; measuring a second dynamic alignment differential between the left eye and the right eye acquiring the second-shifted target with the eye tracker; determining an average dynamic alignment differential from the first dynamic alignment differential and the second alignment differential, optionally with a computer; and determining a prescription prism to reduce the average dynamic alignment differential.

In some embodiments, a method for determining a binocular dynamic alignment can include the following steps: causing a patient to gaze at a starting target with a left eye and a right eye, with a display; dynamically varying a characteristic of the target, with the display; measuring a left-eye dynamic characteristic of the left eye tracking the varying target and a right-eye dynamic characteristic of the right eye tracking the varying target with an eye tracker; determining an average dynamic alignment differential between the left-eye dynamic characteristic and the right-eye dynamic characteristic over the tracking the varying target, with a computer; and determining a prescription prism to reduce the average dynamic alignment differential. In some embodiments, the dynamically varied characteristic of the target is a target position, scanned along a path in one dimension or two dimensions.

In some embodiments, a method for determining a binocular dynamic alignment can include the following steps: causing a patient to gaze at a starting target with a left eye and a right eye, with a display; shifting the target in a direction by a target shift angle at a target shift time, with the display; measuring a dynamic alignment differential between the left eye and the right eye acquiring the shifted target, with an eye tracker and a computer; and determining a prescription prism to reduce the dynamic alignment differential.

In some embodiments, a method for determining an ocular dynamic alignment can include the following steps: presenting a first target for an eye at a first angle at a first time, with a display; measuring a first dynamic response of the eye acquiring the first target, with an eye tracker; presenting a second target at a second angle at a second time, with the display; measuring a second dynamic response of the eye acquiring the second target with the eye tracker; and determining an average dynamic response differential from a difference of the first dynamic response and the second dynamic response, optionally with a computer.

BRIEF DESCRIPTION OF FIGURES

FIGS. 3A-B illustrate a method for determining a binocular dynamic alignment.

FIG. 4A-B illustrate a target shifting protocol.

FIGS. 8A-B illustrate timing diagrams taken with patients.

FIG. 11 illustrates a method for determining a binocular dynamic alignment.

FIGS. 12A-B illustrate additional types of dynamic targets.

FIG. 13 illustrate a method for determining a binocular dynamic alignment.

FIG. 15 illustrate a method for determining an ocular dynamic alignment.

DETAILED DESCRIPTION

The need for identifying additional sources of symptoms associated with ocular misalignment is answered below by exploring dynamical misalignments between the two eyes. Extensive experiments suggested that in a notable fraction of the cases, the symptoms were caused by the movement of the eyes not having been sufficiently coordinated and aligned dynamically.

Of the extraocular muscles, the lateral rectus muscles turn the eyes outward, while the medial rectus muscles turn the eyes inward. In a notable fraction of symptomatic patients, studies found various misalignments and reduced coordination between the lateral rectus and the medial rectus of the two eyes, or generally, between the yoke (d) muscles. These include turning the eyes at different speed, or at different rate of rotation; not moving the eyes along the same linear path; and not acquiring new targets at the same time at the end of a rotation. Since the stimuli coming from the two eyes carry information for how much the heads moves, when to turn, and in general how to change head positions, inconsistent information from the two eyes can cause conflicting signals for the activation and control of the neck muscles. This can lead to neckaches, which in turn can cause headaches and migraines.

An enlightening example is reading. Eye tracking experiments demonstrated that when patients (other than those with speedreading training) read, their eyes acquire the starting point of a word, then quickly scan the word, followed by resting at the end of the word, possibly to give time for the brain to determine the meaning of the word. This is followed by repeating the process for the subsequent word. The entire cycle of acquisition-scan-rest typically takes about 200 ms/word, of which only a fraction is taken up by the scanning itself. In patients, often a difference of several milliseconds was observed between the left eye and the right eye acquiring the starting point of the next word or stopping at the end of the scanning. This difference is a notable few percent of the total scanning time and thus can cause conflict and disorientation on how much to rotate, or move, the eyeballs and the entire head in the process of reading. Since this conflict and disorientation is repeated 200-300 times per minute during reading, it is not so surprising that eventually our visual and muscular system reacts to it with the symptomatology of fatigue and migraines.

Figure 1A:
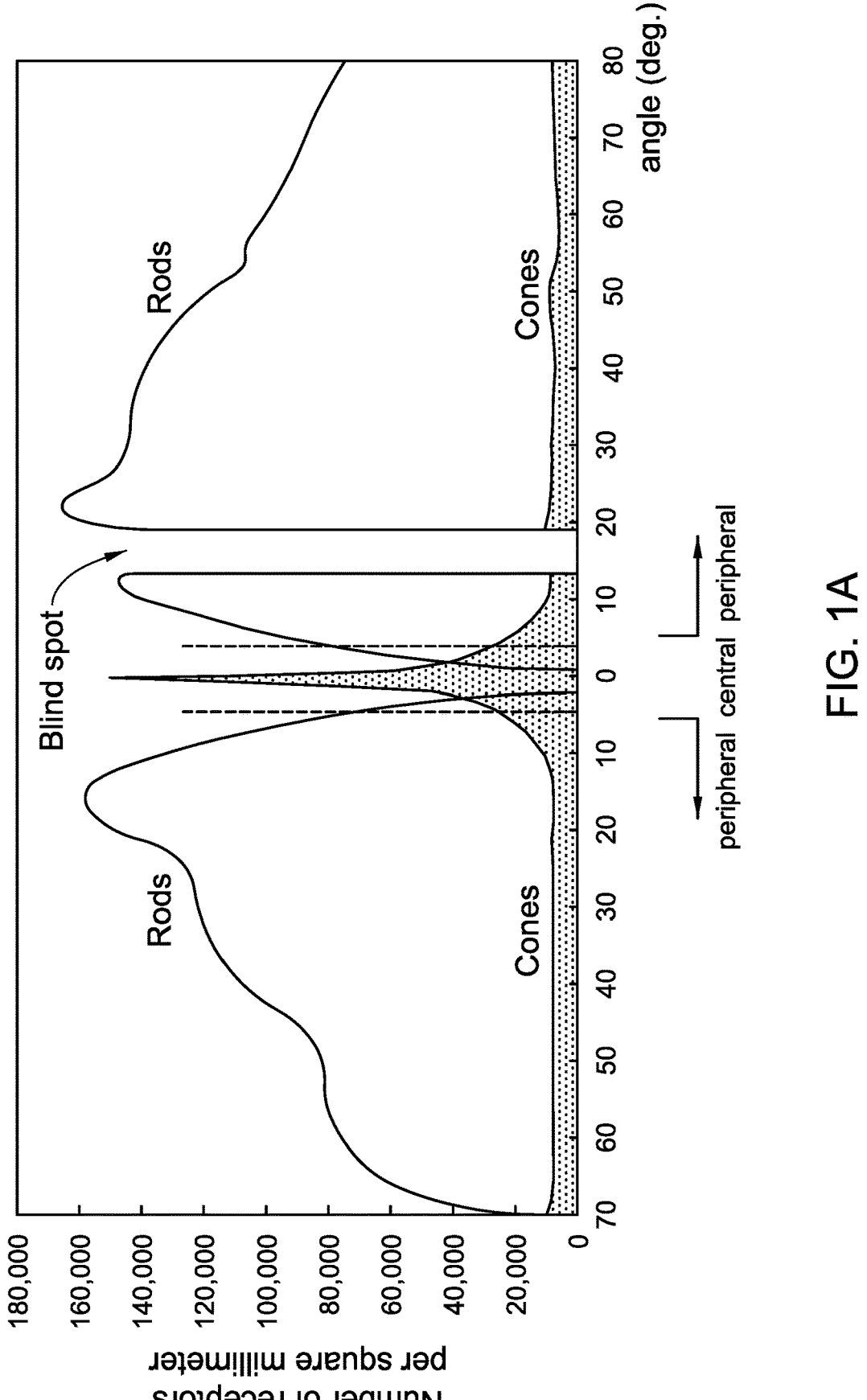
FIGS. 1A-B illustrate aspects of the human vision system.

FIG. 1A illustrates the anatomical reason why there is only a very limited tolerance for such dynamical misalignment in our visual system. The cones that control color vision are tightly concentrated in the central, foveal region. The angular radial extent of this foveal region is only about 2 degrees. Once the eye optical axis is misaligned with the line connecting the eye with a new target beyond these 2 degrees, the visual acuity drops off precipitously. Therefore, every perceived misalignment induces a subsequent corrective rotation and adjustment of the eyes, the head, or both, to re-center the eye's alignment and restore foveal vision.

Remarkably, our eyes perform rapid rotational adjustments even when no obvious stimuli demand it, such as reading. Saccades, or saccadic motion can last 20-200 ms, and can involve very fast rotation of the globes of the eye, up to angular speeds of 100-500 degrees per second. There are multiple propositions why our eyes perform these rapid saccadic motions. One school of thought is that, since there are no rods in the center and very low density of cones at the periphery, the eye constantly makes small rotations so that the nominally centered target gets seen by both cones and rods. Another theory is related to edge recognition. An efficient process to recognize the edges of the objects is to rock the eyes back-and-forth by a few degrees and identify the edges from where this rocking motion induces the sharpest changes.

Besides reading, another activity that requires a high frequency of acquiring new targets is driving. Our peripheral vision continuously recognizes newly emerging targets as the car moves forward at high speed and sends stimuli to the brain asking for rotating the eyes or the head so that the newly emerged targets can be checked whether a reaction is necessary. This is a special case of the general "passing" of newly acquired targets from the peripheral vision to the central vision, every form of which requires coordination between perceptive and muscle-activation functions. This "target passing" is further complicated by the amount of light present which effects pupil size. Decreased lighting generally increases our pupil size, thereby altering the visual depth of focus. A change in the depth of focus changes the eye's ability to calculate the distance the peripheral target is off fovea. Therefore, the pupil size is important in the determination of the alignment differential between the two eyes.

All of the just listed functions necessitate the acquisition of off-center new targets several times a second. However, if the two eyes provide different, conflicting stimuli how far the eyeballs, and the entire head needs to turn to acquire these new targets, this conflict can cause neck tension, fatigue, headaches that can eventually escalate into migraines.

In medical terms, the eyes acquire new targets by executing a peripheral visually guided saccade followed by a pursuit. In engineering terms, the eye/brain system is inherently solving control-theory problems which can be expressed in terms of established mathematics and algorithms. It is helpful to view the eye problems observed as sub-optimal control system performance to discern clues for medical corrective measures.

The visually guided saccade in control-theory terms is a rapid, open loop action by multiple actuators (muscles) whose parameters are estimates derived from the peripheral vision and learned responses. What would be done with numerical calculations in a machine is done by judicious selection in parallel from many associative responses activated in a neural system. Both can work well or poorly. One performance metric in either context is the error vector representing the difference between the optimal and achieved ending eye angles from which to begin the next operation-pursuit.

Following the saccade, the pursuit is slower and achieved with a closed loop (feedback) system. This action requires visual data processing and is computationally intensive in both machine and biological systems. The amount of pursuit final correction required for each eye to achieve its target depends primarily upon the performance quality of its preceding saccade. A machine or biological system can be expected to experience the same control difficulties from compromised saccade performance. In humans, however the magnitude of the saccade error vector, the angular discrepancies between the subsequent pursuit vectors and the timing discrepancies between the pursuit onsets and completions are correlated with patient eye misalignment symptoms.

Figure 1B:
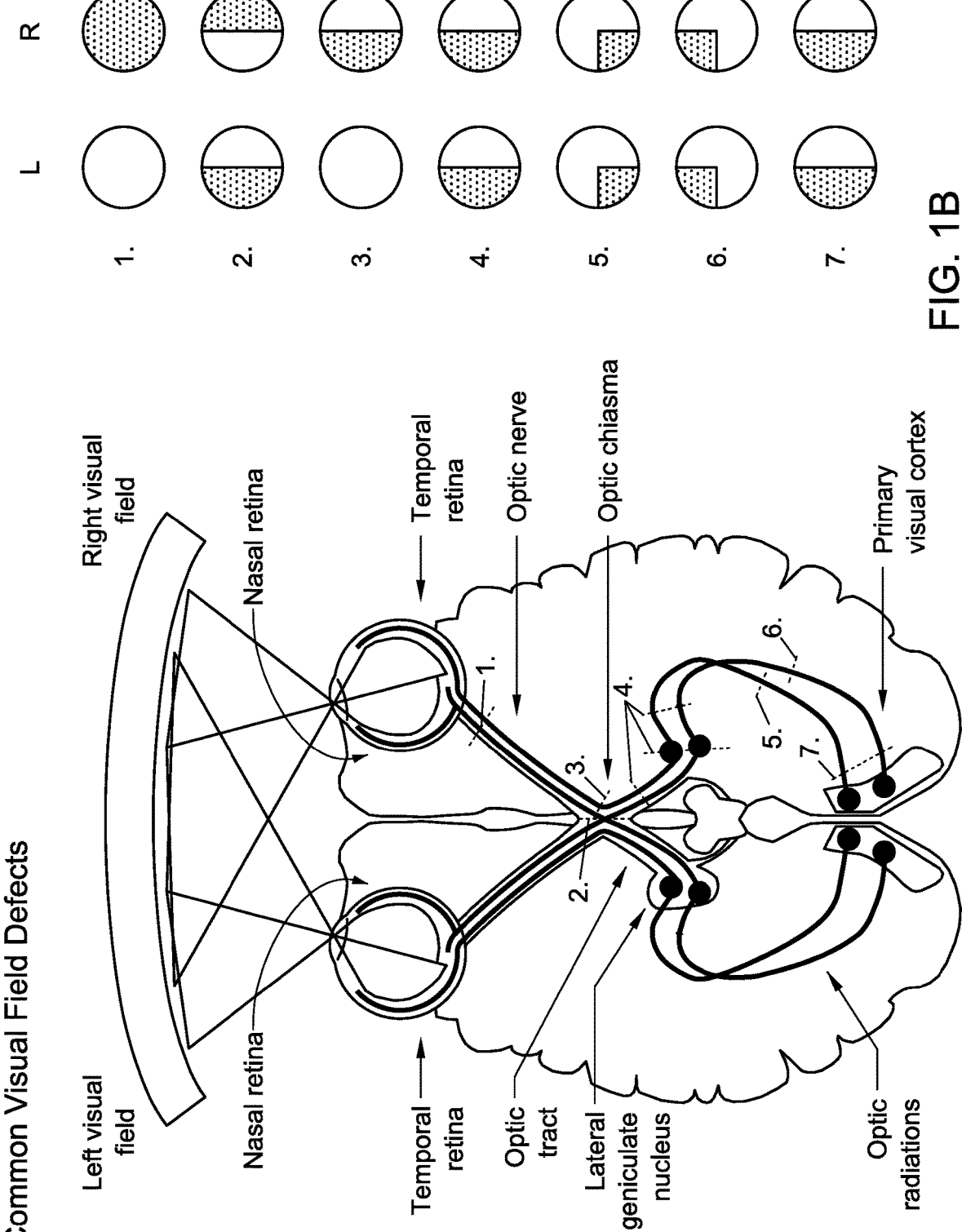

FIG. 1B illustrates one more relevant detail: that the retina has sub-regions, served by different optic nerves which have complex connections along the way between the retina and the visual cortex. In each eye, the temporal retina and the nasal retina are served by different optic nerves. There can be also dynamical differences between the portions of the retina above the equator and below the equator. Finally, as the seven numbered regions show, damage or malfunction at specific points along the optical nerves can lead to visual field defects in specific sub-regions, as also discussed later. Reduced coordination between these sub-regions of the retina can lead to further dynamical misalignments.

Extensive experimentation motivated by the above considerations gave rise to the insight that it may be possible to reduce the above described dynamical misalignments between the eyes by prescription prismatic glasses, and therefore to reduce the confusion and conflict in the stimuli just how much the eye globes need to be rotated by the yoked ocular muscles, as well as how much the neck muscles need to rotate the head to acquire new, off-center targets.

In the following a system and a method will be described for determining such a binocular dynamic alignment. The output of this system and method can be used to determine a prescription for a prismatic lens to reduce a differential of the dynamic alignment, thereby to optimize the binocular dynamic alignment.

Figure 2:
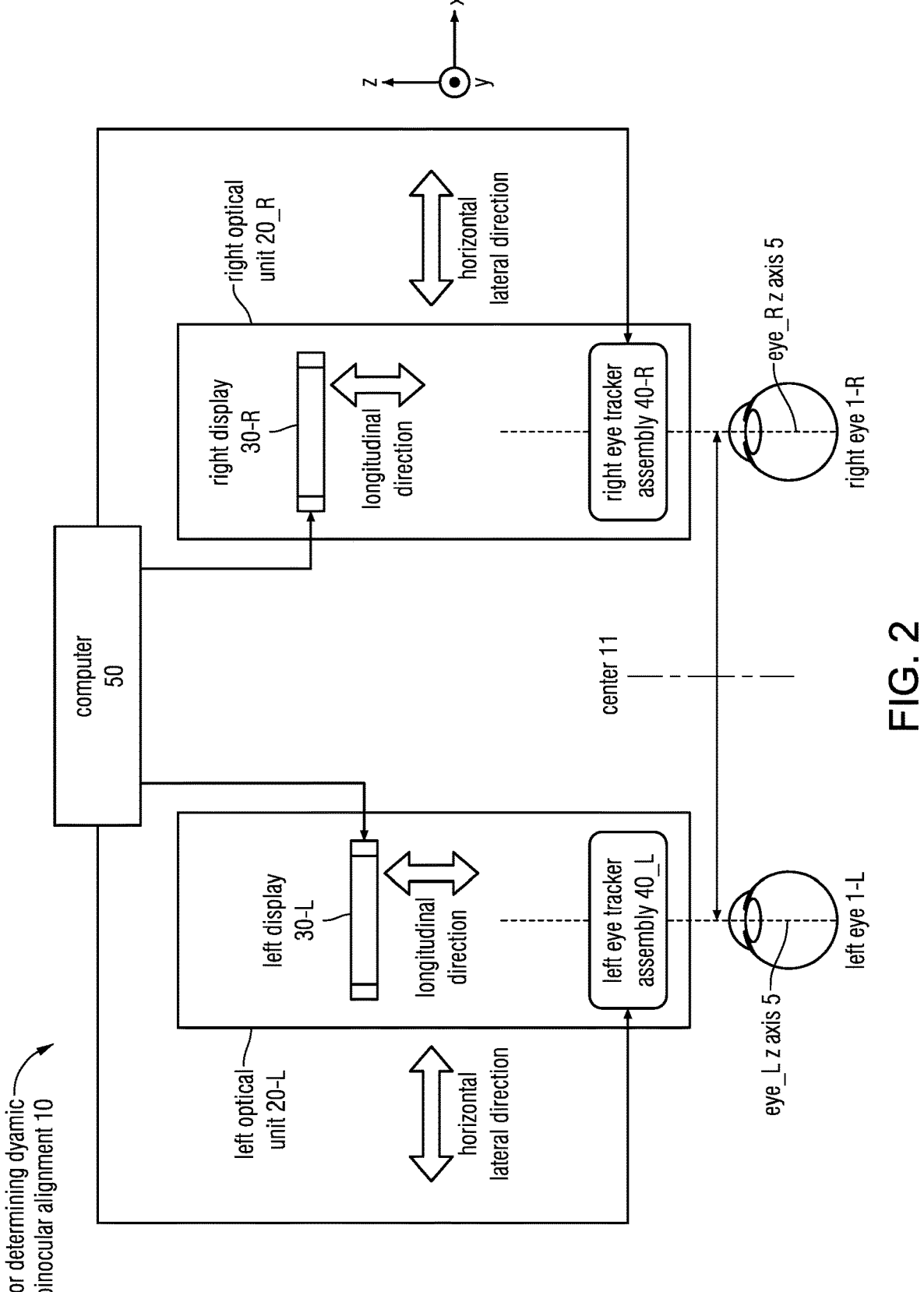
FIG. 2 illustrates a system for determining a dynamic binocular alignment.

FIG. 2 illustrates a system for determining a dynamic binocular alignment differential 10. The system for determining a dynamic binocular alignment 10 can include a left optical unit 20_L that includes a left display 30_L and a left eye tracker 40_L; as well as a right optical unit 20_R that includes a right display 30_R and a right eye tracker 40_R. The left/right displays 30_L/R can be adjustable in a longitudinal direction, along the optical, or z axis 5 of the left eye 1_L and right eye 1_R. This adjustability can be used for simulating a distance of a target, as well as the existing prescription of the patient. Further, the optical units 20_L/R can be laterally adjustable. This adjustability can ensure that the system can be properly aligned for patients who have different pupillary distances from a center 11. Proper alignment makes it possible to use smaller eye tracking optics, thereby reducing the size of the entire system 10. The eye trackers 40_L/R can include infrared (IR) illumination and/ or IR LEDs, whose IR light is reflected from the eye and captured and recorded by IR cameras. In broader terms, the eye trackers 40_L/R can include one or more of an infrared imaging eye tracker, a visible video imaging eye tracker, a pupil size tracker, and a Purkinje-reflection-based eye tracker.

For brevity, the system for determining a dynamic binocular alignment 10 will also be simply referred to as "the system 10" interchangeably. Also for brevity, "a left element xx_L and a right element xx_R" sometimes together will be referenced simply as "elements xx_L/R", or even "element xx".

The eye trackers 40_L/R can partially share the optical path of the system 10, their IR beams redirected from the main optical path in the x or y direction by beam splitters. In other embodiments, the eye trackers 40_L/R can be separately directed at the eyes 1_L/R from an acute angle, without sharing the main optical path. Such designs are used, e.g., in some virtual reality goggles.

In some other embodiments, the position of the displays 30_L/R and the eye trackers 40_L/R can be interchanged: the eye trackers 40_L/R can be positioned along the z axis, and the displays 30_L/R can be positioned laterally off in the x or y direction, facilitated by beam splitters.

Finally, the operation of the system for determining dynamic binocular alignment 10 can be controlled by a computer 50.

The displays 30_L/R can be a wide variety of display systems that are capable of displaying a dynamic target in a stereoscopic manner. Embodiments include an LCD display, an OLED display, a mechanically movable light source such as a LED, a few discrete LEDs, positioned appropriately, or a LED array. As mentioned, the term "the display 30" will be also used to refer to the left display 30_L and the right display 30_R together. The display 30 can be either a pair of displays, such as the display 30_L and the display 30_R, or a single centrally located display 30, where the two halves of the display 30 may be used for displaying dedicated images for the left eye 1_L and for the right eye 1_R.

In other alternative embodiments, the system for determining a dynamic binocular alignment differential 10 can be formed with a single, stereo-capable display 30. The stereo capability can be achieved by several known single display technologies, some listed next.

(1) Active shutter technology: The display presents images for the two eyes sequentially in an alternating manner, while active shutters block the view of the two eyes in a synchronously alternating manner, synchronized with the display. The presently most widely used shutters use a liquid crystal layer which becomes opaque when a voltage is applied to the liquid crystal layer. The timing signal can be relayed to the voltage generator in a wired or a wireless manner.

(2) Polarized light technology: The display presents the images for the two eyes sequentially. An active, switchable polarized filter is placed in front of the display, which filters the alternating displayed images in a synchronously alternating manner along two perpendicular polarization planes. The stereo experience is achieved by having passive polarizers in front of each eyes, oriented into the two polarization planes of the active polarized filter.

(3) Image splitting glass technology: The stereo vision is achieved by the displayed image being split up for the two eyes by a suitable operated glass splitter.

(4) Headset technology: The single display, implemented in a headset, displays separate images for the left eye and for the right eye on the two halves of the display, The separate visual experiences for each eye are secured by a visual divider/separator, positioned perpendicular to the display at the line separating the two halves.

From here on the term "display" will be used in a broad sense and can be implemented with any of the above single display/monitor/screen, or double display/monitor/screen technologies.

In all the above stereo display designs, the illusion of different viewing distances can be generated by various optical techniques, in spite of the physical distance of the display remaining fixed.

FIG. 3A illustrates that with this system for determining dynamic binocular alignment 10, a method for determining a binocular dynamic alignment 100 can include the following steps:

causing 110 a patient to gaze at a starting target with a left eye and a right eye, with a display;

shifting 120 the target in a first direction by a first target shift angle at a first target shift time, with the display;

measuring 130 a first dynamic alignment differential between the left eye and the right eye acquiring the first-shifted target, with an eye tracker;

shifting 140 the first-shifted target in a second direction at a second target shift time, with the display;

measuring 150 a second dynamic alignment differential between the left eye and the right eye acquiring the second-shifted target with the eye tracker; and determining 160 an average dynamic alignment differential from the first dynamic alignment differential and the second alignment differential, with a computer. These steps will be described in detail below.

The determining 160 of an average dynamic alignment differential can be followed by a determining 170 of a prescription prism to reduce the average dynamic alignment differential. This last step can be performed either by the system 10, by the computer 50 of the system, or by a qualified medical personnel, such as an optician or an optometric technician.

FIG. 4A illustrates the causing step 110. A target 32 can be presented centrally for the left eye 1_L and the right eye 1_R. Here an embodiment with a single display 30 is shown. In other embodiments, separate displays 30_L and 30_R can be employed, that, together, create the perception of a single target 32. For clarity, in the subsequent FIGS. 4-6 the display 30 is suppressed. Optical axes 60_L/R of the left/right eyes can be defined in several different ways. One of them is the straight line going through the center of the globe of the left and right eyes and the center of their crystalline lens. The angle these optical axes 60_L/R make with the z axes 5 (dead ahead) of the left/right eyes will be called left optical axis angle 62_L and right optical axis angle 62_R. In step 110 the starting target 32 can be presented centrally, as shown, or at a starting offset angle. In some displays this may be accomplished by presenting a single LED source, visible for both eyes 1_L/R. In other embodiments, each eye can only see its own LCD display, as in FIG. 2. The left and right displays 30_L/R can each display the starting target 32, such as a shiny dot or cross, positioned such that they create the impression of a single target 32 located at some distance because the left and right eyes 1_L/R fuse their images into the perception of a single target 32. The target 32 can have additional characteristics, such as it can be an extended object, whose size, luminosity and/or color can be varied.

FIG. 4B illustrates the shifting step 120. Method 100 includes shifting the target 32 in a first direction by a first target shift angle TSA 64_1 at a first target shift time TST_1, with the display 30_L/R. As mentioned before, "the display" can refer to a single source display, such as a single LED, or a pair of displays, such as the LCD displays 30_L/R, or any of the above display embodiments. The target shift angle TSA 64_1 is defined by the target z axis ("dead ahead") and the target chord connecting the center 11 and the first-shifted target 32_1, as shown. The shift of the first-shifted target 32_1 can be characterized equivalently not only by the target shift angle TSA 64_1, but by a target shift distance, or by any other suitable measure. FIG. 4B illustrates the moment in time, t=TST_1, when the first-shifted target 32_1 has been shifted, but the eyes 1_L/R did not react to this shift yet.

Figures 5A, 5B:
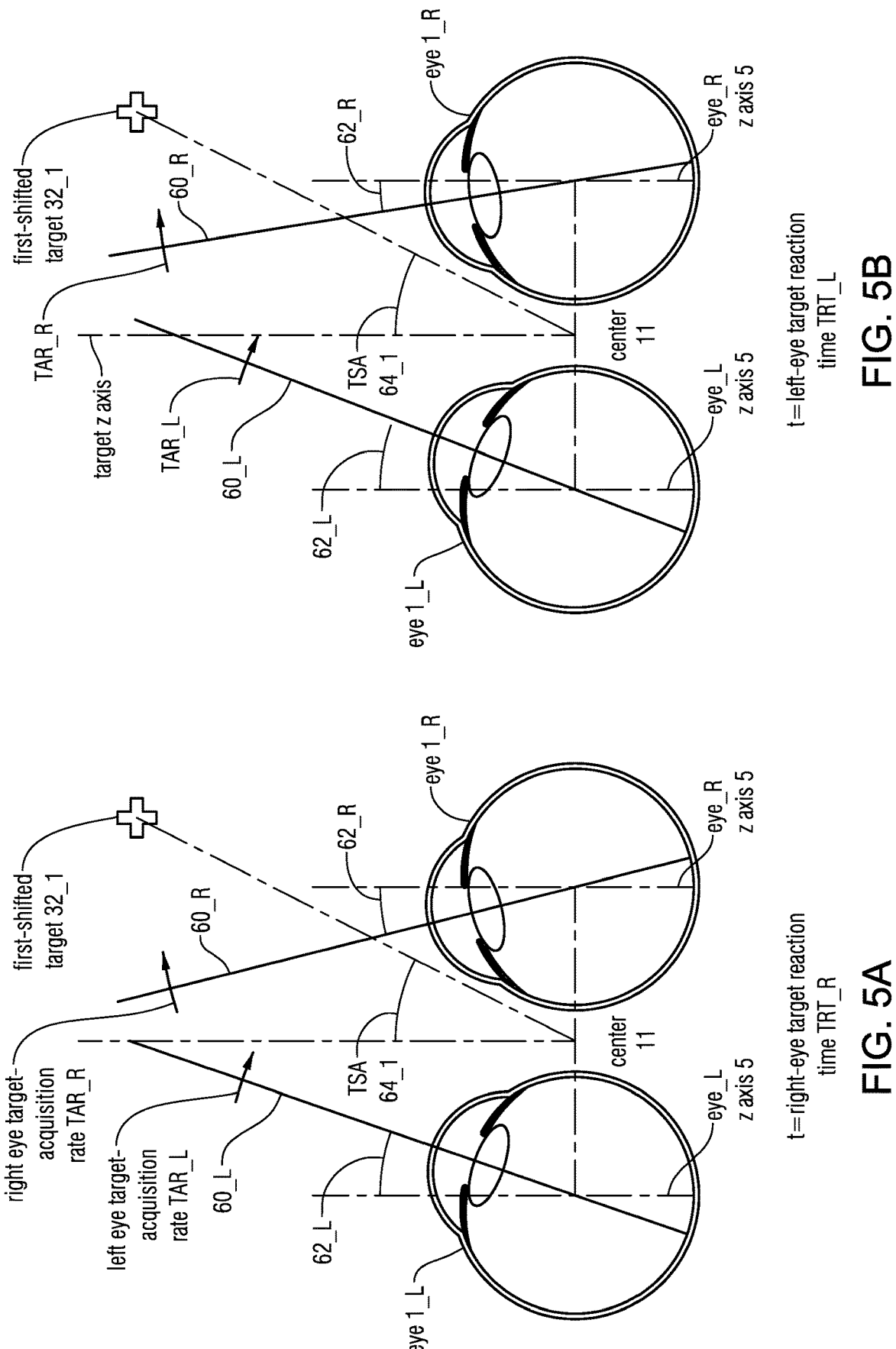
FIGS. 5A-C illustrate the response by a left eye and a right eye for the target shifting.

FIG. 5A illustrates a time shortly after t=TST_1, when at least one of the eyes started to react to the shifting of the first-shifted target 32_1. This will be referenced as right-eye target reaction time TRT_R. For some patients, their right eye 1_R will react first, for others, their left eye 1_L. For the same patient, if the target is shifted in a different direction, the left eye 1_L may react before the right eye 1_R. For concreteness, and to avoid convoluted language, the measurement will be described for the case when the right eye 1_R reacted first. However, this should not be construed as a limitation, in cases where the left eye 1_L reacts first, the language of the description should be adapted with the obvious modifications.

FIG. 5A illustrates that at time t=TRT_R, the right eye 1_R and its right optical axis 60_R reacted to the shifting 110 of the first-shifted target 32 by rotating away from the starting direction and towards the first-shifted target 32_1. FIG. 5B illustrates the moment in time t=TRT_L when the left eye 1_L also reacted to the target shift and started rotating towards the first-shifted target 32_1.

Figures 6A, 6B:
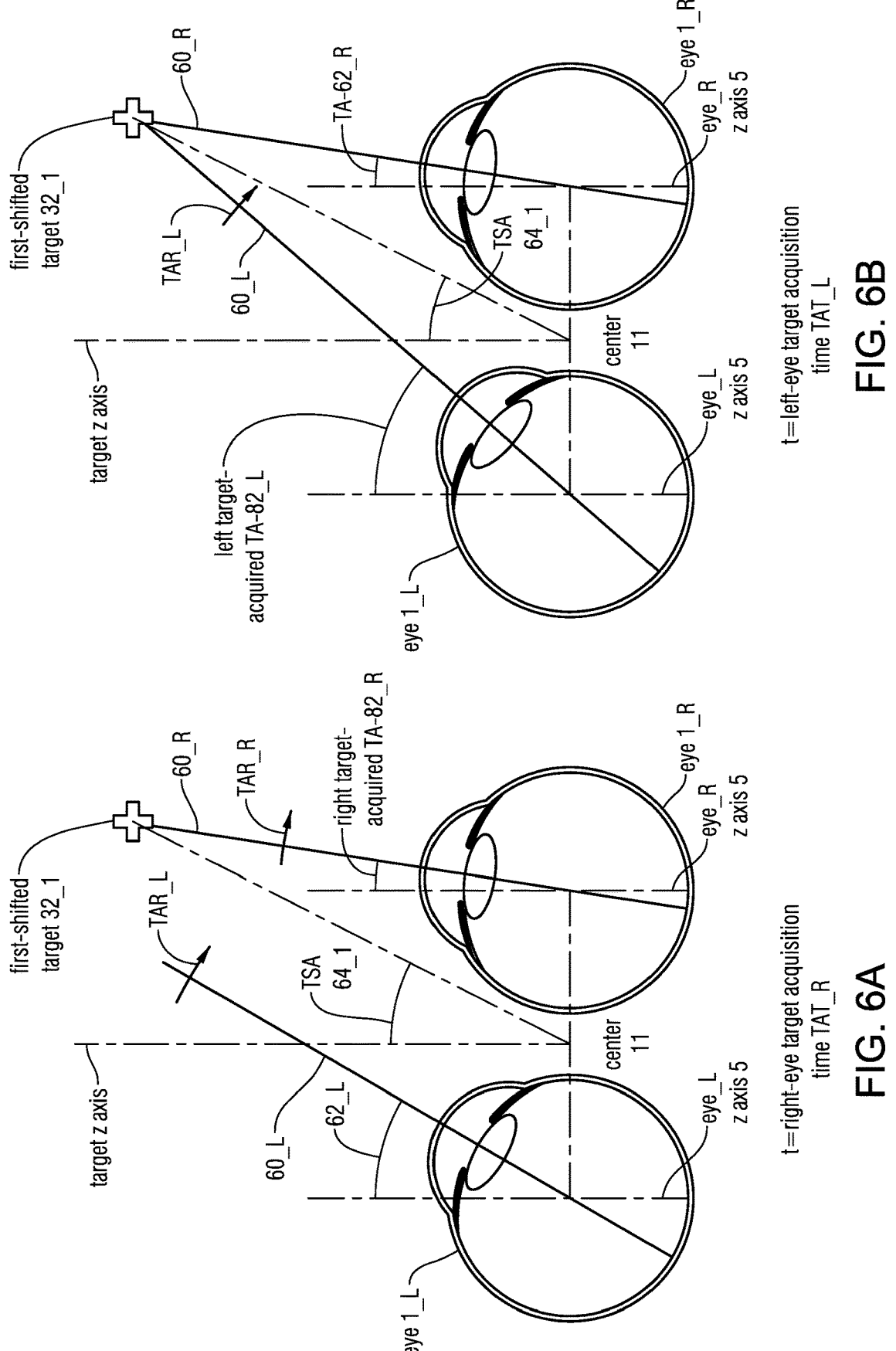
FIGS. 6A-B illustrate a response by a left eye and a right eye for the target shifting.

FIGS. 5A-B illustrate what was elaborated in the introduction: the left eye 1_L and the right eye 1_R typically do not react to a dynamic target shift in the same manner. The reaction can be different in different ways. In some cases, the Target Reaction Times can be different: $TRT_L \neq TRT_R$. In other cases, target acquisition rates TAR_L/R, the angular speed of the rotation of the eye optical axis angles 62_L/R can be different: $TAR_L \neq TAR_R$. FIGS. 6A_B illustrate that in yet other cases, target acquisition times TAT_L/R, the times at which the eye optical axes 60_L/R acquire the direction of the first-shifted target 32_1 can be different: $TAT_L \neq TAT_R$.

Figure 5C:
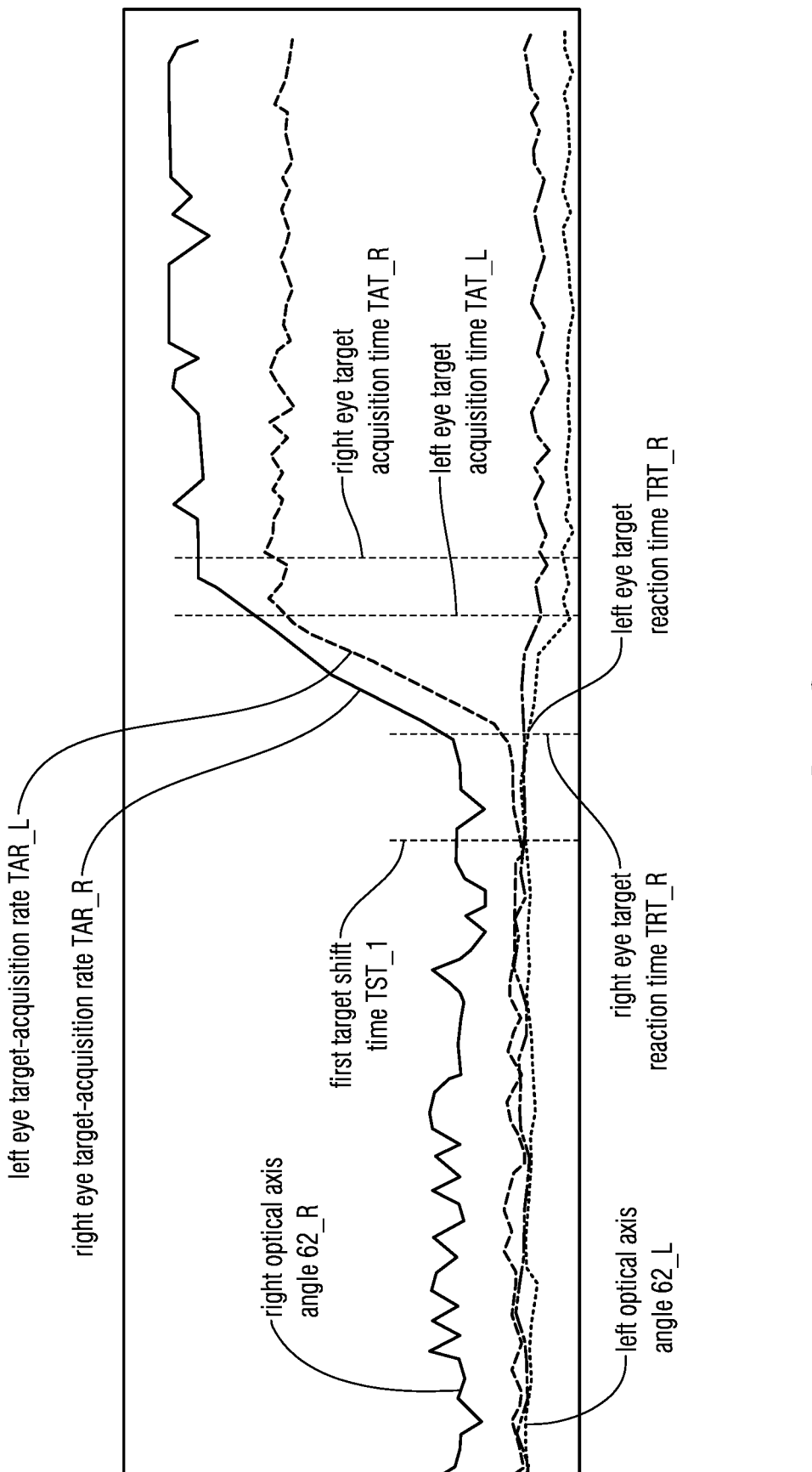

FIG. 5C illustrates the eye tracker 40_L/R having recorded the time-dependent optical axis angles 62_L/R of a patient after the first target shift time t=TST_1. For this patient, the target reaction times were the same: TRT_L=TRT_R. However, the target acquisition rates, directly related to the slopes of the eye tracking curves, were different: $TAR_L \neq TAR_R$. These different acquisition rates caused that the target acquisition times were also different: $TAT_L \neq TAT_R$.

As mentioned above, FIGS. 6A-B illustrate the target acquisition times TAT_L/R, the times at which the eye optical axes 60_L/R acquired the direction of the first-shifted target 32_1. FIG. 6A illustrates the time t=TAT_R when the right eye 1_R acquired the first-shifted target 32_1, but the left eye 1_L did not do so yet. This acquired angle is referred to as right-eye target acquired optical axis angle TA-62_R. FIG. 6B illustrates the later time t=TAT_L, when the left eye 1_L also acquired the first-shifted target 32_1 with a left eye target acquired optical axis angle TA-62_L. FIG. 5C illustrates the result of the eye tracking of a real patient's eyes, showing that these two times can be different: $TAT_L \neq TAT_R$. As discussed earlier, this difference in this case is connected to the left and right target acquisition rates being different: $TAR_L \neq TAR_R$. Therefore, even though the left and right eyes 1_L/R reacted to the first-shifting of the target 32 at the same time, TRT_L=TRT_R, because of the different target acquisition rates the two eyes acquire the target at different target acquisition times: $TAT_L \neq TAT_R$.

Figure 7:
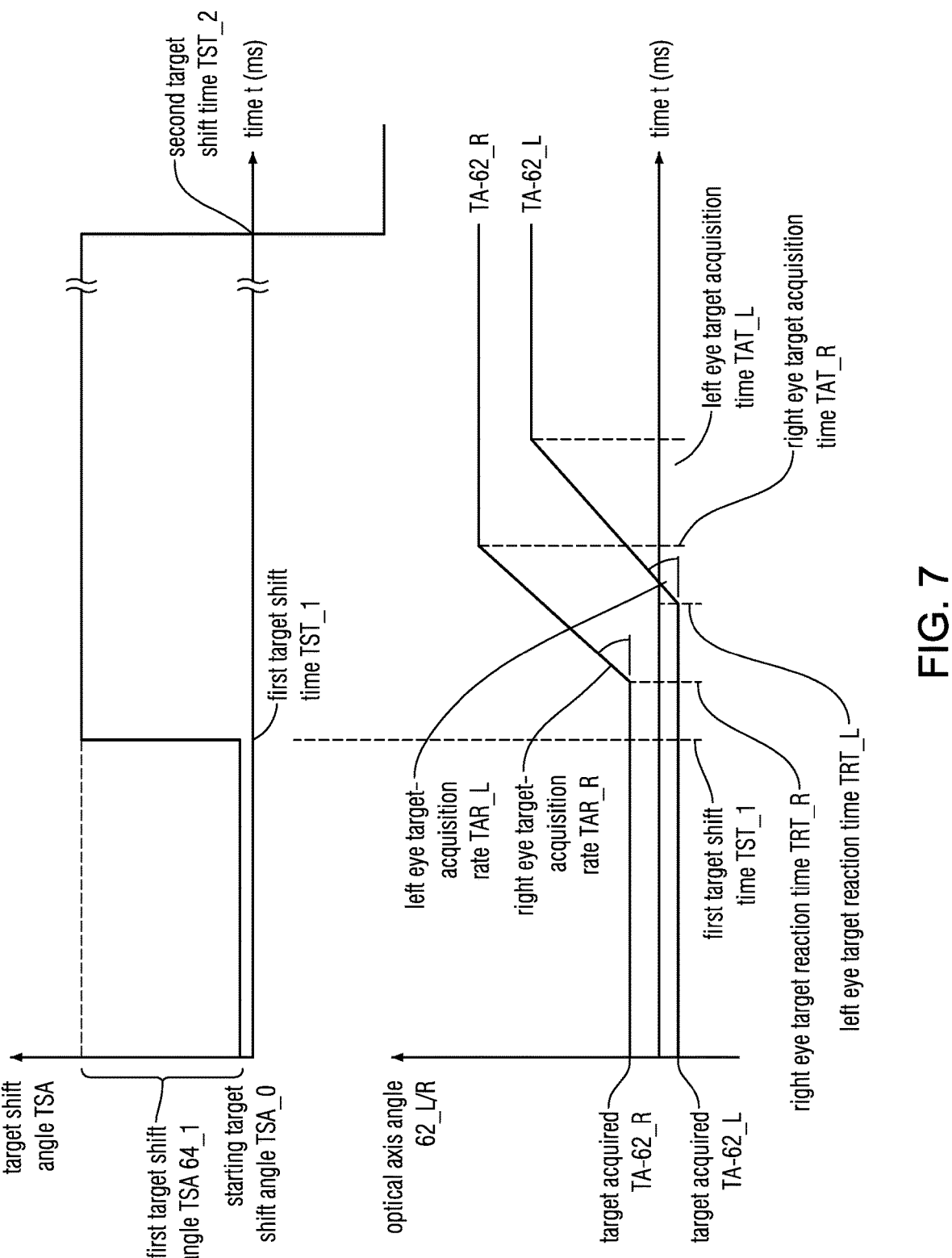
FIG. 7 illustrates the timing diagram of the left eye and the right eye.

FIG. 7 summarizes these concepts on a single timing diagram. The upper panel shows the timing diagram of the target shift angle TSA 64_1 relating to the first shift at TST_1. At the first target shift time TST_1, the starting target angle is shifted to a first target shift angle TSA 64_1. This shift can be abrupt or gradual, as explained later. The starting target shift angle TSA_0 is typically zero, as the target 32 is typically central (on the target z axis) in the beginning of the method 100. However, various considerations can motivate the trained professional to start from a non-zero starting target shift angle TSA_0. For example, as discussed in relation to FIGS. 8A-B, the starting target shift angle TSA_0 can be the same, or close to, the second target shift angle TSA 64_2.

The lower panel of FIG. 7 shows that the reaction of each eye can be characterized by at least three characteristics: the left eye target reaction time TRT_L, the left eye target acquisition rate TAR_L, and the left eye target acquisition time TAT_L; and the same three characteristics for the right eye: TRT_R. TAR_R, and TAT_R. In FIG. 7, all three of these characteristics are different for the left eye 1_L and the right eye 1_R.

At the start, the optical axis angles 62_L/R are the angles corresponding to the two eyes having acquired the starting target 32. Using the earlier notation, these are the target acquired optical axis angles, or TA-62_L/R. In the case of a simple, centered starting target 32, these two angles are symmetric around zero: TA-62_L=−(TA-62_R). This case is shown in FIG. 7. Of course, the starting target can be presented in a non-centered position. Also, the patient may have a static binocular misalignment. In each of these cases, the two starting angles TA-62_L and TA-62_R can be asymmetric. Further, well after the first target shift time TST_1, both eyes have once again acquired the first-shifted target 32_1. Thus, the ending angles can be once again denoted TA-62_L/R_1, as shown, but now they refer to the eyes 1_L/R having acquired the first-shifted target 32_1.

With these considerations, in some embodiments the measuring 130 of the first dynamic alignment differential can include measuring the first dynamic alignment differential as a first target reaction time differential ΔTRT_1, related to a difference of a right eye target reaction time TRT_R and a left eye target reaction time TRT_L. In a formula, $$\Delta TRT\_1 = TRT\_R - TRT\_L. \tag{1}$$

This first target reaction time differential is a measure of the dynamic misalignment between the right eye 1_R and the left eye 1_L regarding shifting the target 32 in a first direction.

FIG. 3B illustrates the corresponding sub-steps of the measuring step 130 as follows:

determining 132 a left eye optical axis angle 62_L and a right eye optical axis angle 62_R before, or around, the first target shift time TST_1;

measuring 134 the left eye target reaction time TRT_L as the time representing the left eye optical axis angle 62_L reacting to the shifting of the first-shifted target 32_1;

measuring 136 the right eye target reaction time TRT_R as the time representing the right eye optical axis angle 62_R reacting to the shifting of the first-shifted target 32_1; and determining 138 a first target reaction time differential ΔTRT_1 as a difference of the right eye target reaction time and the left eye target reaction time: ΔTRT_1=TRT_R-TRT_L.

FIG. 7 also illustrates the second shifting step 140. Once the first target reaction time differential ΔTRT_1 has been determined, the first-shifted target 32_1 can be shifted for a second time by a second target shift angle TSA 64_2 at a second target shift time TST_2 to the second shifted target 32_2, in order to determine a dynamic misalignment of the two eyes in a second direction. In a typical embodiment, the first direction can be the positive x direction, or a positive angle rotation, while the second direction can be the negative x direction, or a negative angle rotation. In some embodiments, the first shift 120 and the second shift 140 can be symmetric. E.g. the first target shift angle TSA 64_1 can be +α, while the second target shift angle TSA 64_2 can be −α, both rotations aligned with the x, or horizontal axis, wherein α can be in the α=5 degrees-50 degrees range, in some embodiments in the α=10 degrees-30 degrees range. Many other embodiments are possible, such as asymmetric shifting, and the directions of the first shifting and the second shifting not being aligned with each other, such as at least one of the shifts having a y component.

The measuring step 150 can, subsequently, include repeating steps 132-138 relating to the second-shifting 140 of the target 32 in the second direction in order to determine a second target reaction time differential ΔTRT_2=TRT_R-TRT_L. The timing diagram of the second shifting 140 is essentially analogous to FIG. 7, the timing diagram of the first shifting 120, with the natural changes of the indices from "1" to "2", as appropriate. As such, it would be repetitive and cumulative to show this second shifting timing diagram here.

The determining step 160 involves determining the average dynamic alignment differential ΔTRT, related to an average of the first target reaction time differential ΔTRT_1 (determined in step 130) and the second target reaction time differential ΔTRT_2 (determined in step 150). In some embodiments, this average dynamic alignment differential ΔTRT can be simply the average, or sum of the first target reaction time differential ΔTRT_1 and the second target reaction time differential ΔTRT_2:

$$\Delta TRT = (\Delta TRT\_1 + \Delta TRT\_2)/2 \tag{2}$$

Note that this equation (2) is sensitive to the signs of ΔTRT_1 and ΔTRT_2. If the first target reaction time differential ΔTRT_1 is positive (i.e. the right eye reacts later, TRT_R>TRT_L) and the second target reaction time differential ΔTRT_2 is equal in magnitude and opposite in sign (i.e. negative, the left eye reacts later), then ΔTRT=0. Dynamic misalignments with a zero average dynamic alignment differential ΔTRT are harder to correct with a static prism prescription. However, if ΔTRT is non-zero, then there is an overall bias between the dynamics of the two eyes. Such overall bias can be the consequence, for example, by the weakness of at least one of the yoked muscles relating to coordination of the two eyes 1_L/R. Such muscle weakness is sometimes referred to as ophthalmoplegia, which can be affected by different diseases such as myasthenia gravis. For example, if the right eye tracks right-shifting targets quicker than the left eye, whereas the two eyes track left-shifting targets with about the same speed, then prescribing a spectacle with a prism that at least partially compensates the difference for right-shifting targets will reduce the dynamic misalignment between the eyes. Determining and prescribing glasses with such a prism is an embodiment of the determining step 170.

FIGS. 8A-B illustrate that such asymmetries in the dynamic alignment of the eyes are quite common. FIG. 8A top panel shows the timing diagram of the optical axis angles 62_L/R, in response to the target 32 being shifted from a TSA 64_0=−15 degrees to TSA 64_1=+15 degrees. The timing diagram was obtained by repeating the target shifting 5 times back and forth between −15 degrees to +15 degrees and determining the average target reaction times of the patient ΔTRT_1 and ΔTRT_2, in order to determine a statistically reliable target reaction time differential ΔTRT= (ΔTRT_1+ΔTRT_2)/2. Visibly, on average the left eye 1_L reacted to the target shift 1.2 ms later than the right eye 1_R. With the above sign convention of subtracting the left eye target reaction time TRT_L from the right eye target reaction time TRT_R. this means a first target reaction time differential ΔTRT_1=−1.2 ms. The bottom panel shows the same angles 62_L/R when the target was moved the opposite direction, from TSA 64_1=+15 degrees to TSA 64_2=−15 degrees. Here the left eye was faster, and with an asymmetrically larger amount: by a second target reaction time differential ΔTRT_2=+4.5 ms. Therefore, the average target reaction time differential was given by:

$$\Delta TRT = (\Delta TRT\_1 + \Delta TRT\_2)/2 = (4.5 \text{ ms} - 1.2 \text{ ms})/2 = +1.6 \text{ ms}.$$

Because of the asymmetry between the reactions to the right-shifting targets and the left-shifting targets, a spectacle that (at least partially) compensates this average dynamic alignment differential with a prism prescription can improve the patient's overall dynamic binocular visual acuity.

There can be different considerations that set the specific details of the prescription prism. If there is a dynamic alignment differential between the left and right eyes, e.g., the left eye reacts to shifting targets slower than the right eye, then a prism can be prescribed for one or both eyes that alters the direction of the eye optical axes 60_L/R to at least partially compensate for this dynamic alignment differential by changing the dynamic movement and timing between yoked muscles. The prescribed prism will prompt the slower, left eye to track the shifting target differently. Embodiments of a prescription prism can include a training glass, a vision therapy, with glasses, lighted stimulators, or with virtual reality goggles that influence the eye-rotating muscles to turn in unison. Over time, treatments and therapies with the above embodiments of prescription prisms were capable of improving the dynamic alignment of the eyes. In cases when none of these treatments or therapies worked, the prescription of prismatic glasses proved to bring symptom relief.

In some embodiments, the measuring 130 can include the measuring of the first dynamic alignment differential as the first target acquisition rate differential ΔTAR_1, related to a difference of the right eye target acquisition rate TAR_R, and the left eye target acquisition rate TAR_L as $$\Delta TAR\_1 = TAR\_R - TAR\_L. \qquad (3)$$

As before, after the measuring 130 has been performed for the target 32 having shifted in a first direction, in shifting step 140 the first-shifted target 32_1 can be shifted by a second target shift angle TSA 64_2 for a second time at a second target shift time TST_2 into a second-shifted target 32_2, in order to determine a dynamic misalignment of the two eyes in a second direction. This can be followed by the measuring step 150, where the measuring step 130 is repeated, but for the second-shifting of the target 32_2. The result of the measuring step 150 is a second target acquisition rate differential ΔTAR_2, related to a difference of the right eye target acquisition rate TAR_R, and the left eye target acquisition rate TAR_L as ΔTAR_2=TAR_R-TAR_L. Finally, in the determining step 160, an average of the first and second target acquisition rate differentials can be taken to determine the average target acquisition rate differential ΔTAR:

$$\Delta TAR = (\Delta TAR\_1 + \Delta TAR\_2)/2 \qquad (4)$$

In the determining step 170, ΔTAR can be used as the average dynamic alignment differential, in analogy to ΔTRT in the earlier description, to prescribe a prismatic lens to reduce this ΔTAR target reaction time differential.

FIG. 5C illustrates an eye tracking chart of a patient, where the left and right eye target acquisition rates TAR_L/ R, measured by the slopes of the left and right eye tracking curves, are visibly different for the left and right eyes 1_L/R. An analogous case can be seen in the eye tracking timing diagrams of FIGS. 8A-B. The duration of the middle, target tracking intervals TTI_L/R between the target reaction time TRT_L/R and the target acquisition time TAT_L/R is given by TTI_L/R=|TAT_L/R-TRT_L/R|. The target acquisition rate TAR is given by the inverse of this TTI_L/R: TAR_L/ R=Target Shift Angle*(TTI_L/R)$^{-1}$. The longer the target tracking interval TTI_L/R, the lower the target acquisition rate TAR_L/R. Visibly, in FIG. 8A, where the target shift angle changes from −15.5 degree to +15.5 degree, i.e. TSA 64_1=31 degrees for the first, right-shifting target, TAR_R=31 deg*(30.3 ms)$^{-1}$=31 deg*0.033 ms$^{-1}$, TAR_L=31 deg*(20.6 ms)$^{-1}$=31 deg*0.048 ms$^{-1}$. Accordingly, ΔTAR_1=TAR_R-TAR_L=−31 deg*0.015 ms$^{-1}$=− 0.46 deg/ms. For the left-shifting target ΔTAR_2=TAR_R- TAR_L=31 deg*(18.2 ms)$^{-1}$−31 deg*(21.2 ms)$^{-1}$=31 deg*0.055 ms$^{-1}$−31 deg*0.047 ms$^{-1}$=31 deg*0.008 ms$^{-1}$=0.25 deg/ms.

The average target acquisition rate differential, determined in step 160, ΔTAR=(ΔTAR_1+ΔTAR_2)/2=(−0.46 deg/ms+0.25 deg/ms)/2=−0.10 deg/ms.

Finally, in some embodiments, the measuring 130 the first dynamic alignment differential can include measuring the first dynamic alignment differential as a first target acquisition time differential, related to a difference of a left eye target acquisition time TAT_L and a right eye target acquisition time TAT_R.

In more detail, the measuring 130 in this embodiment can include the following sub steps, in analogy with sub steps 132-138, in FIG. 3B:

determining 132' a left eye optical axis angle 62_L and a right eye optical axis angle 62_R before, or around, the first target shift time TST_1;

measuring 134' the left eye target acquisition time TAT_L as the time representing the left eye optical axis angle 62_L acquiring the first-shifted target 32_1;

measuring 136' the right eye target acquisition time TAT_R as the time representing the right eye optical axis angle 62_R acquiring the first-shifted target 32_1; and determining 138' a first target acquisition time differential ΔTAT_1 as a difference of the right eye target acquisition time TAT_R and the left eye target acquisition time TAT_L:

$$\Delta TAT\_1 = TAT\_R - TAT\_L \qquad (5)$$

These substeps can be then followed by the second shifting 140 of the first-shifted target 32_1 by the second target shift angle TSA_2 at the second target shifting time TST_2 and repeating the substeps 132'-138' of the measuring step 130 as substeps of the measuring step 150 for this second-shifted target 32_2.

Finally, in the determining step 160, an average of the first and second target acquisition times differentials can be taken to determine the average target acquisition time differential ΔTAT:

$$\Delta TAT = (\Delta TAT\_1 + \Delta TAT\_2)/2 \qquad (6)$$

In the determining step 170, ΔTAT can be used as the average dynamic alignment differential, in analogy to ΔTRT and ΔTAR in the earlier descriptions.

In the above embodiments, the average target reaction time differential ΔTRT, the average target acquisition rate differential ΔTAR, and the average target acquisition time differential ΔTAT are three embodiments of the average dynamic alignment differential, determined in the determining step 160. Each of these embodiments can be used in the determining step 170 for determining a prescription prism to reduce the average dynamic alignment differential. Additional embodiments of the average dynamic alignment differential will be described next.

Figures 9A, 9B:
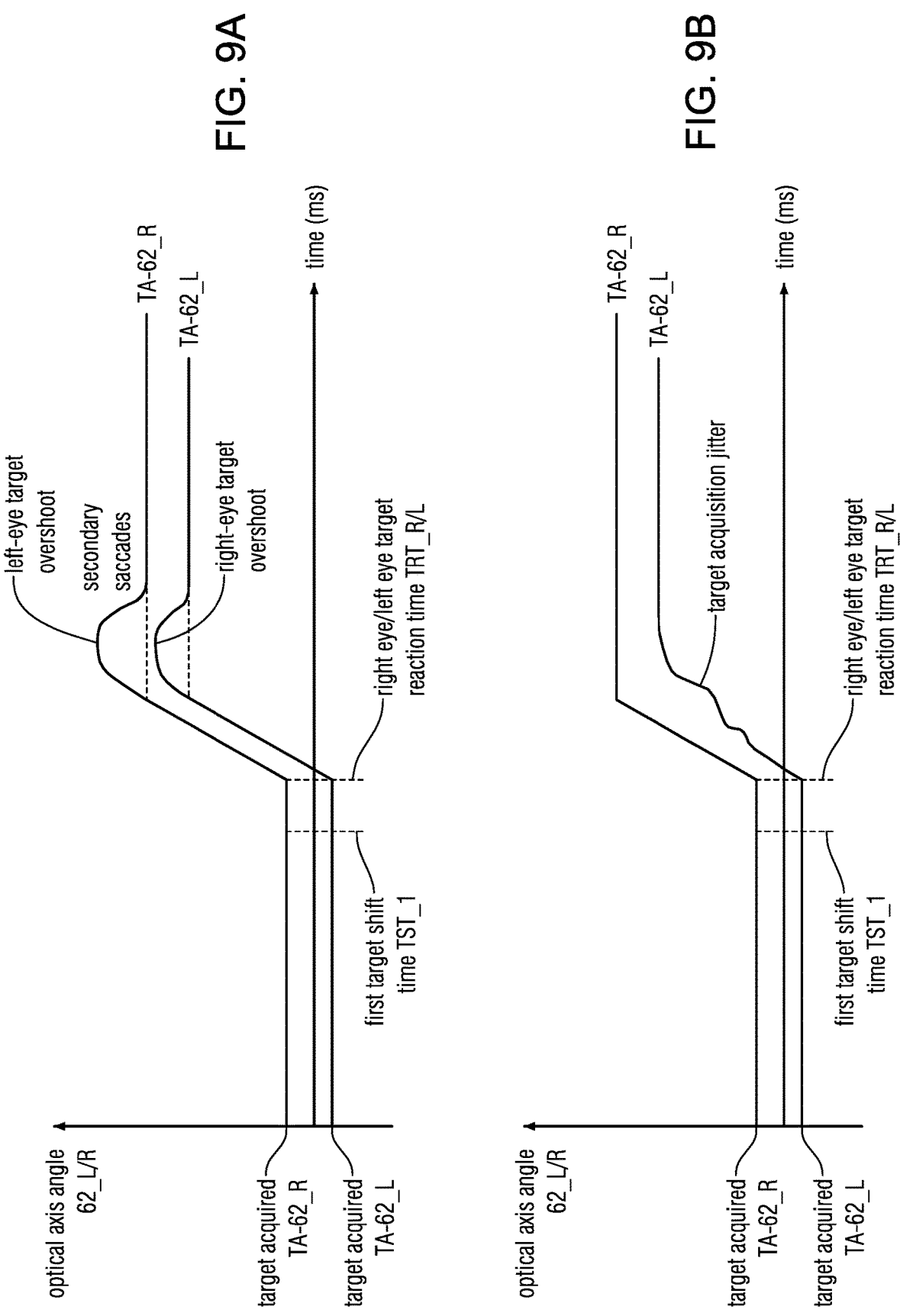
FIGS. 9A-B illustrate additional types of the average dynamic alignment differential.

FIGS. 9A-B illustrate additional embodiments of the measuring 130 of the first dynamic alignment differential, comprising:

(1) determining a left eye optical axis angle 62_L and a right eye optical axis angle 62_R before, or around, the first target shift time TST_1;

(2) measuring a left eye target overshoot TOS_L related to a maximum angle with which the left eye optical axis angle 62_L overshoots the first-shifted target 32_1;

(3) measuring a right eye target overshoot TOS_R related to a maximum angle with which the right eye optical axis angle 62_R overshoots the first-shifted target 32_1; and (4) determining a first target overshoot differential $\Delta$TOS_1 as a difference of the right eye target overshoot and the left eye target overshoot:

$$\Delta TOS\_1 = TOS\_R - TOS\_L \qquad (7)$$

In this embodiment, the dynamical alignment differential is related not to a difference of characteristic times, but to another characteristic of the dynamical target tracking by the eyes: that the eye optical axes 60_L/R, as they move to acquire the first-shifted target 32_1, often overshoot, as shown in FIG. 9A. The overshoot is then subsequently corrected in so-called secondary saccades, eventually aligning the left/right eye optical axis angles 62_L/R to point at the first-shifted target 32_1 at the first target shift angle TSA 64_1. If the overshoot is different for the two eyes $TOS_L \neq TOS_R$, their difference can be referred to as "target overshoot differential" $\Delta$TOS_1=TOS_R-TOS_L. This target overshoot differential $\Delta$TOS_1 is yet another dynamical misalignment, where reducing $\Delta$TOS_1 and thereby inducing dynamically more aligned tracking by the two eyes brings benefits for the patient's dynamical visual acuity. As before, one of the clearest examples of when and how this target overshoot differential hinders dynamic visual acuity is by reflecting on the process of reading: when a patient's eyes are jumping from one word to the next, if the eyes overshoot the beginning of the next word, the brain has to wait until both eyes eventually settle on where the next word begins. If the overshoot differs for the two eyes, it is even more demanding for the brain to coordinate the process of starting to scan the next word from its beginning. Finally, as before, in the determining step 160, an average of the first and second target overshoot differentials corresponding to the target shifting in the first and in the second directions, can be taken to determine the average target overshoot differential $\Delta$TOS:

$$\Delta TOS = (\Delta TOS\_1 + \Delta TOS\_2)/2 \qquad (8)$$

FIG. 9B illustrates yet another embodiment of dynamical misalignment. Here, instead of overshooting, the eyes 1_L/R "undershoot", i.e. track the first-shifted target 32_1 partially, then stop, then continue to track, often repeating several times until they acquire the first-shifted target 32_1 properly. This process can be called target acquisition jitter, or TAJ. Alternatively, this jitter can be called target acquisition drift, or target pursuit. As before, if one of the eyes exhibits a different amount of "target acquisition jitter" than the other eye, this "target acquisition jitter differential" is another form of dynamical misalignment, the reduction of which improves the dynamical visual acuity. There can be many different embodiments of the measuring 130 of the target acquisition jitter TAJ, including: calculating a derivative, or slope, of the eye as it is tracking the first-shifted target 32, from TRT_L/R to TAT_L/R, and characterizing how much the derivative deviates from its average value during the target acquisition. In other embodiments, the measuring 130 of the first dynamic alignment differential can include measuring a functional characteristic of the left eye and the right eye tracking the target, wherein the functional characteristic is constructed from at least one of a jitter, a lag, a curvature, an S-shape curvature, and a higher derivative.

As before, a first target acquisition jitter differential $\Delta$TAJ_1 can be determined as a difference of the right eye target acquisition jitter TAJ_R and the left eye target acquisition jitter TAJ_L:

$$\Delta TAJ\_1 = TAJ\_R - TAJ\_L \qquad (9)$$

Finally, as before, in the determining step 160, an average of the first and second target acquisitions jitters differentials can be taken to determine the average target acquisition jitter differential $\Delta$TAJ:

$$\Delta TAJ = (\Delta TAJ\_1 + \Delta TAJ\_2)/2 \qquad (10)$$

In all of the above embodiments of the method 100, the determining 160 of an average dynamic alignment differential from the first dynamic alignment differential and the second alignment differential can also include assigning different weights to the first dynamic alignment differential than to the second alignment differential. For example, the above equations that calculate embodiments of the average dynamic alignment differential can be modified as follows:

$$\Delta TRT = \alpha\Delta TRT\_1 + (1-\alpha)\Delta TRT\_2 \qquad (2')$$
$$\Delta TAR = \alpha\Delta TAR\_1 + (1-\alpha)\Delta TAR\_2 \qquad (4')$$
$$\Delta TAT = \alpha\Delta TAT\_1 + (1-\alpha)\Delta TAT\_2 \qquad (6')$$
$$\Delta TOS = \alpha\Delta TOS\_1 + (1-\alpha)\Delta TOS\_2 \qquad (8')$$
$$\Delta TAJ = \alpha\Delta TAJ\_1 + (1-\alpha)\Delta TAJ\_2 \qquad (10')$$

where $\alpha$ can be in a range of [0,1]. These embodiments are informed by the lens design consideration that some patients may have a lifestyle or occupation which make the patient use his/her eyes to track targets that shift more often in one direction. The most obvious example is patients for whom reading is important, since reading requires acquiring/tracking targets that systematically shift from the left to the right, since the target shifting takes the form of repeatedly targeting the next word that is to the right of the previously targeted word. For such patients, the determining 160 of the average dynamic alignment differential in equations (2'), (4'), (6'), (8'), and (10') may involve choosing an $\alpha$ value different from $\alpha$=0.5 that places more emphasis on reducing the alignment differential related to shifting the target from left to right.

Several of the described embodiments of the method 100 included symmetric shifting of the target 32. For example, in FIG. 8A, the target 32 was shifted from 15 degrees to the left to 15 degrees to the right, in FIG. 8B from 11 degrees to the left to 11 degrees to the right, approximately. But a wide variety of other arrangements can be also practiced within the method 100. For example, initially the target 32 can be centrally located, the first-shifting 120 can be a center-to-periphery shift, and the second-shifting 140 can be a periphery-to-center shift. In broader terms, in some embodiments, one of the first-shifted target and the second-shifted target can be more central than the other target.

In yet other embodiments, one of the first-shifted target and the second-shifted target differs from the starting target in a characteristic other than the target shift angle, including a size, a color, a light intensity, or a shape. For example, as the target is first-shifted in the first-shifting step 120, its color can also change. Or its shape or size can also change. In a notable embodiment, as discussed before, since on one hand the pupil size reacts to the strength of the illumination, and on the other hand, the pupil size impacts the depth of focus that may influence the dynamical alignment differential, the shifting of the target 32 can be accompanied with the changing of the target luminosity.

Because of the importance of the pupil size, some embodiments of the method 100 can include selecting a light intensity of the target 32 to impact a pupil size and thereby a depth of focus of the left and right eyes 1_L/R; measuring the pupil sizes, optionally with a pupil size tracker that can be part of the eye trackers 40_L/R, or possibly a separate module; recording the measured pupil sizes along with the average dynamic alignment differential; and optionally repeating the preceding steps with a different light intensity.

Different light intensities induce different pupil sizes, and different pupil sizes can cause different average dynamic alignment differentials. The light intensity-pupil size dependent dynamic alignment differentials can be used in different ways by medical and ophthalmic professionals. In some cases, prismatic spectacles can be prescribed based on the dynamic alignment differential determined in the lighting conditions most relevant for the patient. For example, for truck drivers who drive a lot at night, or for night guards, the method 100 can be performed at appropriately low light intensities most relevant for their work, and the prescription prism can be determined accordingly. And in reverse, people who work in bright light conditions can be diagnosed by the method 100 at appropriately high light intensities. Further, for some patients who work in varying lighting conditions, the method 100 can be performed at a low light intensity, then repeated at a high light intensity. These two measurements may produce two different dynamic alignment differentials. The optometrist then may choose to form an average dynamic alignment differential from these two values, possibly with some uneven weighting factors, and prescribe a prismatic spectacle based on this averaged dynamic alignment differential. As also discussed, in some cases the optometrist, or ophthalmologist can choose to prescribe not prismatic spectacles, but a vision therapy for the patient based on the determined averaged dynamic alignment differential.

Figures 10A, 10B:
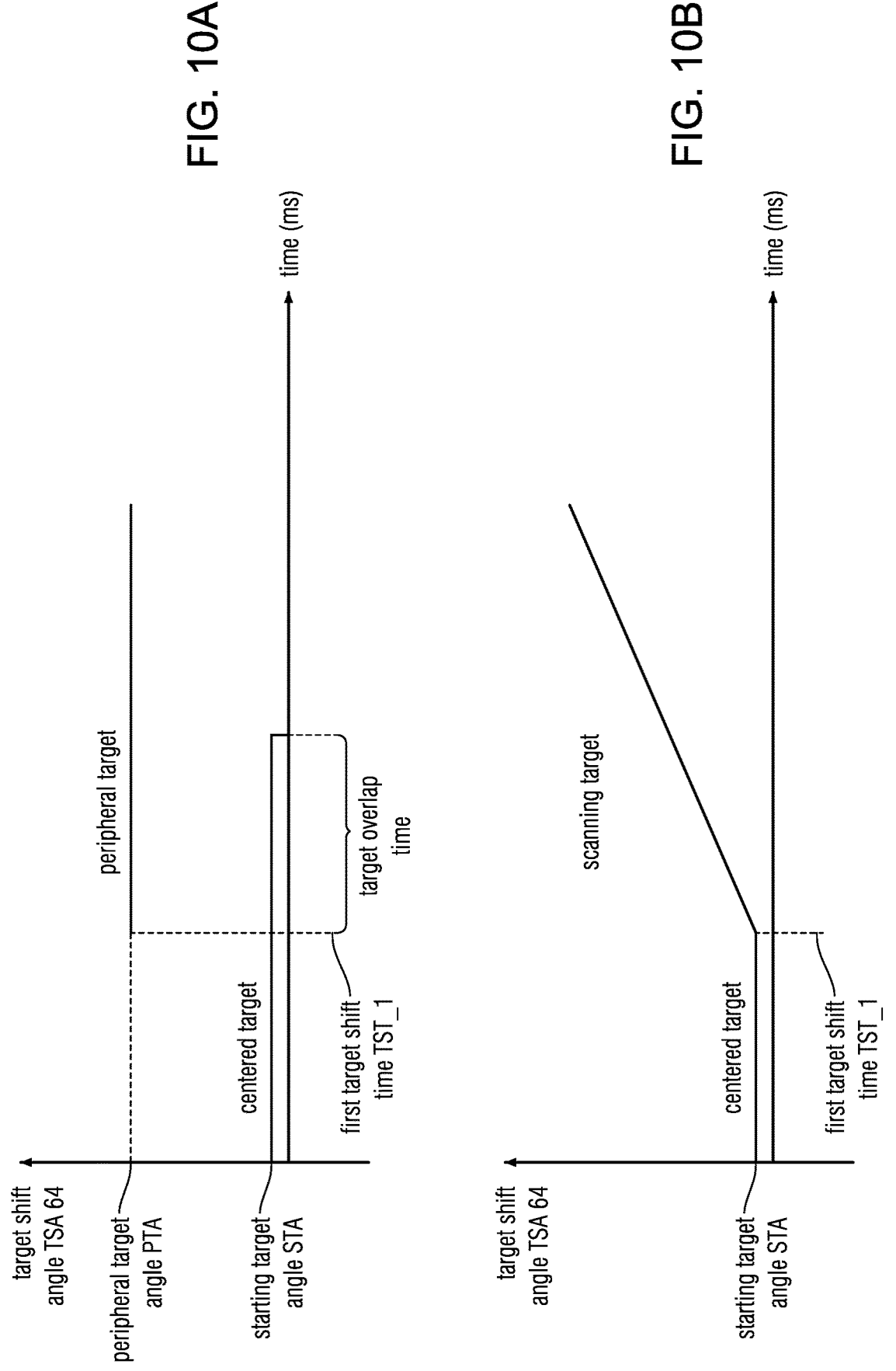
FIGS. 10A-B illustrate additional types of a dynamic target.

FIG. 10A illustrates that in some embodiments, the shifting 120 of the target 32 in the first direction by a first target shift angle TSA 64_1 is performed at the first target shift time TST_1 by presenting a target at the first target shift angle TSA 64_1, possibly with a gradually increasing light intensity, while simultaneously gradually decreasing a light intensity of the starting target at the starting target angle STA. In other words, in these embodiments when the first-shifted target is presented at the first target shift angle TSA 64_1 on the displays 30_L/R, the starting target is not discontinued in a sharp, step-like manner, but, rather, is gradually dimmed away over a target overlap time, as shown.

FIG. 10B illustrates that while in some embodiments the first-shifting 120 of the target 32 in the first direction by a first target shift angle 64_1 can be performed in the above-described step-like manner, in other embodiments the first shifting 120 can be performed in a non-step-like, gradual manner, including in a scanning manner. For example, the target 32 can be continuously shifted from an initial target angle, or location, to a final first-shifted angle or location, as shown in FIG. 10B.

Referring back to FIG. 1B, the human visual fields system is extremely structured and can be broken down into four major quadrants: superior temporal, inferior temporal, superior nasal, and inferior nasal. There are coordinating fields between the eye. For example: the superior temporal field of the right eye corresponds to the superior nasal field of the left eye. The dynamic movement between the eyes can be different in the related visual field quadrants. This can effect the function between the eyes since different visual nerves serve these quadrants. This difference can also be related to usage patterns. For example, patients typically use the lower quadrants for navigating as when we are walking or running and for near-distance activities, such as reading. Therefore, for some patients, the dynamical alignment differential can be different for distant targets where the peripheral targets appear in one quadrant (typically upper) of the visual field, and for near-distance activities, where the peripheral new targets appear in the lower quadrant of the visual field. To treat or mitigate different dynamic alignment differentials in different quadrants and distances, some prismatic lenses can be designed where the determining 170 of a prescription prism involves prescribing different prisms for the upper and lower parts of the lens. Such embodiments of the method 100 can involve performing the method for the target being shifted in an upper hemisphere of a viewing/visual field of the patient to identify an upper average dynamic alignment differential—typically associated with distance viewing; performing the method for the target being shifted in a lower hemisphere of the viewing/visual field of the patient to identify a lower average dynamic alignment differential—typically for near viewing; and determining an upper prescription prism and a lower prescription prism. This can be followed by prescribing a spectacle lens that has a contour, or progressive, prism that varies from the upper prescription prism to the lower prescription prism. In other embodiments, this prism can also be prescribed and formed to compensate for the dynamic alignment differential found between any of the four quadrants.

In a typical example, in some patients the method 100 can be first carried out by presenting targets at a far apparent distance, ending with the determination of a "distance dynamic alignment differential". Next, the method 100 can be repeated with presenting targets at an apparent near distance, leading to the determination of a "near dynamic alignment differential". In a substantial fraction of patients, the distance and near dynamic alignment differentials are different. For such patients, prescribing a contour, or progressive prismatic lens, whose prism value varies from the distance vision region to the near vision region can be the most helpful.

FIG. 11 illustrates a method 200 for determining a binocular dynamic alignment, the method comprising:

causing 210 a patient to gaze at a starting target with a left eye and a right eye, with a display;

dynamically varying 220 a characteristic of the target, with the display;

measuring 230 a left-eye dynamic characteristic of the left eye tracking the varying target and a right-eye dynamic characteristic of the right eye tracking the varying target with an eye tracker; and determining 240 an average dynamic alignment differential between the left-eye dynamic characteristic and the right-eye dynamic characteristic over the tracking the varying target, with a computer.

This can be followed by determining 250 a prescription prism to reduce the average dynamic alignment differential. Embodiments of the method 200 are closely related to the method 100, and thus can be practiced in conjunction with all the details, limitations and features described for the method 100 previously.

FIGS. 12A-B illustrate that in some embodiments of the method 200, the dynamically varied characteristic of the target can be a target position, scanned along a path in one dimension or two dimensions. FIG. 12A illustrates an embodiment of the method 200, wherein the target 32 is moved, or shifted, in a one-dimensional pattern, but instead of a step like shift from a first target shift angle TSA 64_1 to a second target shift angle TSA 64_2, the target is smoothly moving between endpoints, in an oscillatory manner.

FIG. 12B illustrates another embodiment of the method 200, where the target is moving not along a one-dimensional pattern, but along a two-dimensional pattern, such as in a circular motion, shown in the inset. This circular motion can be characterized by two oscillatory target shift angles TSA_x and TSA_y, which are phase-shifted relative to each other by 90 degrees, as shown.

FIG. 13 illustrates a related method 300 for determining a binocular dynamic alignment, the method comprising:

causing 310 a patient to gaze at a starting target with a left eye and a right eye, with a display;

shifting 320 the target in a direction by a target shift angle at a target shift time, with the display; and measuring 330 a dynamic alignment differential between the left eye and the right eye acquiring the shifted target, with an eye tracker and optionally with a computer.

This can be followed by determining 340 a prescription prism to reduce the dynamic alignment differential.

Embodiments of this method 300 can be employed, for example, to design prismatic lenses for patients when there is reason to believe that the dynamic alignment differential can be well-captured by measuring the reaction of the left eye and the right eye to a single shift of the target 32, instead of the two shifts of the method 100. Embodiments of the method 300 can be practiced in conjunction with all the details, limitations and features described for the methods 100 and 200.

For completeness, we return to FIG. 2 for a description of the system for determining a binocular dynamic alignment 10 that can include, a display 30_L/R, for causing a patient to gaze at a starting target 32 with a left eye 1_L and a right eye 1_R; and for shifting the target 32 in a first direction by a first target shift angle TSA 64_1 at a first target shift time TST_1; an eye tracker 40_L/R, for measuring a first dynamic alignment differential between the left eye 1_L and the right eye 1_R acquiring the first-shifted target 32_1; the display 30_L/R being configured for shifting the first-shifted target 32_1 in a second direction by a second target shift angle TSA 64_2 at a second target shift time TST_2; the eye tracker 40_L/R being configured for measuring a second dynamic alignment differential between the left eye 1_L and the right eye 1_R acquiring the second-shifted target 32_2; and an optional computer 50, for determining an average dynamic alignment differential from the first dynamic alignment differential and the second alignment differential.

Figure 14:
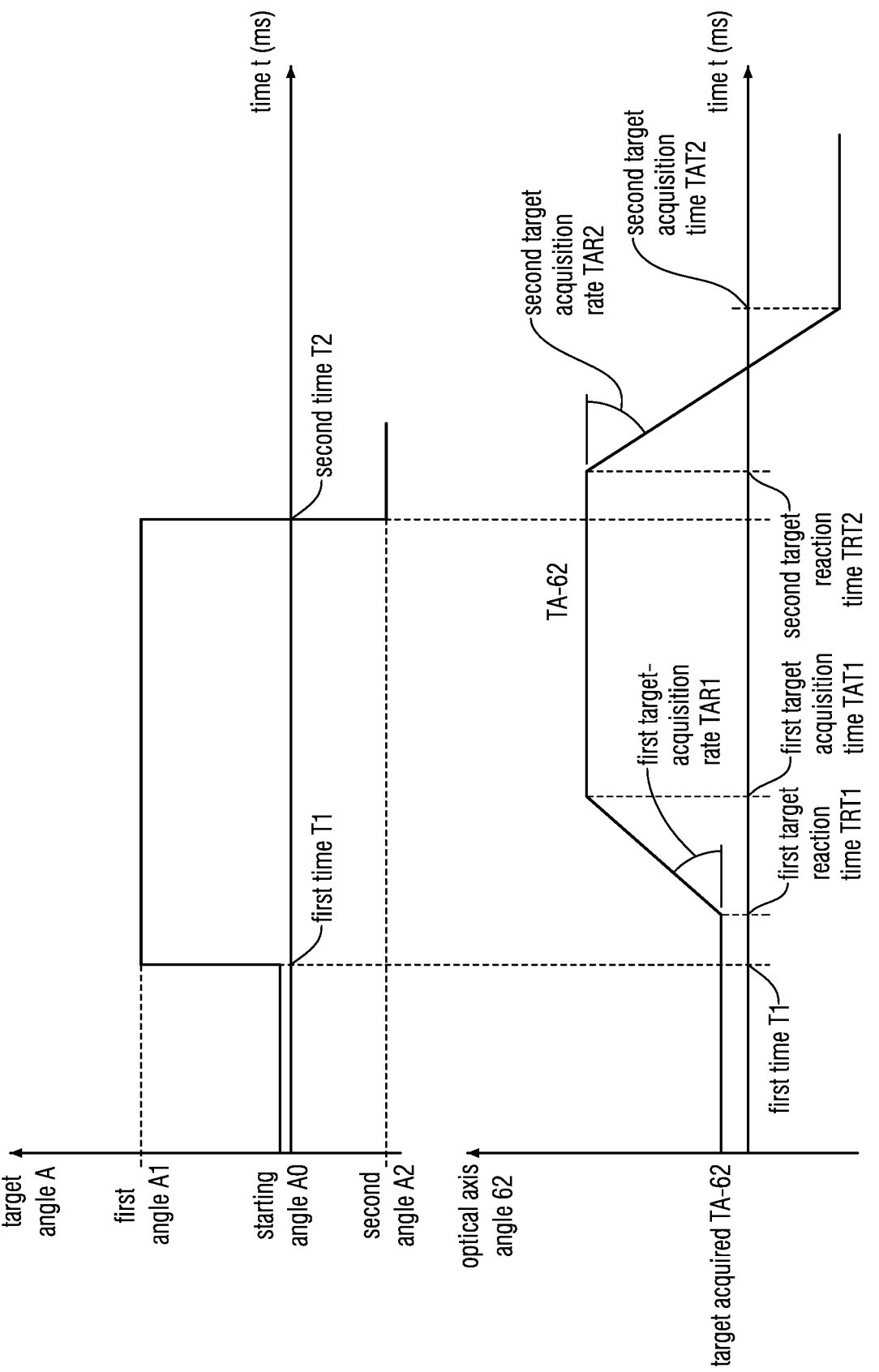
FIG. 14 illustrate the timing diagram of a method for determining an ocular dynamic alignment.

FIGS. 14-15 illustrate yet another method 400 for determining an ocular dynamic alignment, the method comprising:

presenting 410 a first target for an eye at a first angle at a first time, with a display;

measuring 420 a first dynamic response of the eye acquiring the first target, with an eye tracker;

presenting 430 a second target at a second angle at a second time, with the display;

measuring 440 a second dynamic response of the eye acquiring the second target with the eye tracker; and determining 450 a dynamic response differential from a difference of the first dynamic response and the second dynamic response, optionally with a computer.

Embodiments of the method 400 differ from embodiments of the method 100 and the method 300 in that the method 400 is a monocular method-the first target and the second target are presented for one eye. Then a dynamic response differential of that one eye is determined and a vision therapy, or a prismatic glass, may be prescribed to alleviate this dynamic response differential. In a particularly simple embodiment, if the eye reacts asymmetrically, and acquires new targets a bit more easily in one direction than in the other direction, then a prismatic prescription may mitigate this asymmetry. In fact, these embodiments of the previously described methods can be arranged in the following simple table:

TABLE 1

|  | method for one eye/monocular | method for both eyes/binocular |
|---|---|---|
| shift target in one direction |  | method 300 |
| shift target in both directions | method 400 | method 100 |

Each of these methods 100, 300 and 400 can diagnose various asymmetries, misalignments, and differentials of the eye, or eyes, which in many patients can be mitigated by quantitative measurements, followed by a prescription of prismatic glasses.

Continuing the description of the method 400, FIG. 14 illustrates the timing diagram of embodiments of the method 400. This diagram is similar to FIG. 7. FIG. 14 is simpler in the sense that it only shows the optical axis angles of one eye, but it is more extensive in that it shows both the first target presentation time T1 and the second target presentation time T2.

In some embodiments, the measuring 420 of the first dynamic response includes measuring a first target reaction time TRT1; and the measuring 440 of the second dynamic response includes measuring a second target reaction time TRT2.

In some embodiments, the measuring 420 of the first dynamic response includes measuring a first target acquisition rate TAR1; and the measuring 440 of the second dynamic response includes measuring a second target acquisition rate TAR2.

In yet other embodiments, the measuring 420 of the first dynamic response includes measuring a first target acquisition time TAT1; and the measuring 440 of the second dynamic response includes measuring a second target acquisition time TAT2.

In a way reminiscent to the method 100, the determining 450 of the dynamic response differential from a difference of the first dynamic response and the second dynamic response can include determining at least one of the following:

$$\Delta TRT = TRT1 - TRT2 \qquad (11)$$

$$\Delta TAR = TAR1 - TAR2 \qquad (12)$$

$$\Delta TAT = TAT1 - TAT2 \qquad (13)$$

Any one of these differentials can be used to indicate a dynamic response differential for an eye's reaction to target shifting, or acquisition, in different directions, followed by calculating or determining a vision therapy or a prescription prismatic glass.

While this document contains many specifics, these should not be construed as limitations on the scope of an invention or of what may be claimed, but rather as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

The invention claimed is:

1. A method for determining a binocular dynamic alignment, the method comprising:
(1) causing a patient to gaze at a starting target with a left eye and a right eye, with a display;
(2) shifting the target in a first direction by a first target shift angle at a first target shift time, with the display;
(3) measuring a first dynamic alignment differential between the left eye and the right eye acquiring the first-shifted target, with an eye tracker;
(4) shifting the first-shifted target in a second direction by a second target shift angle at a second target shift time, with the display;
(5) measuring a second dynamic alignment differential between the left eye and the right eye acquiring the second-shifted target with the eye tracker;
(6) determining an average dynamic alignment differential from the first dynamic alignment differential and the second alignment differential with a computer; and
repeating at least steps (2)-(5), wherein
the alignment differential is determined based on at least one of a target reaction time, a target acquisition rate, and a target acquisition time of the left eye and the right eye.

2. The method of claim 1, the measuring the first dynamic alignment differential comprising:
measuring the first dynamic alignment differential as a first target reaction time differential, related to a difference of a left eye target reaction time and a right eye target reaction time.

3. The method of claim 2, the measuring comprising:
(1) determining a left eye optical axis angle and a right eye optical axis angle before, or around, the first target shift time;

(2) measuring the left eye target reaction time as the time representing the left eye optical axis angle reacting to the shifting of the first-shifted target;
(3) measuring the right eye target reaction time as the time representing the right eye optical axis angle reacting to the shifting of the first-shifted target; and
(4) determining a first target reaction time differential as a difference of the right eye target reaction time and the left eye target reaction time.

4. The method of claim 3, further comprising:
repeating steps (1)-(4) as part of the measuring of the second dynamic alignment differential, relating to the second-shifting of the target by a second target shift angle in the second direction in order to determine a second target reaction time differential; and
determining the average dynamic alignment differential related to an average of the first target reaction time differential and the second target reaction time differential.

5. The method of claim 1, the measuring the first dynamic alignment differential comprising:
measuring a first target acquisition rate differential, related to a difference of a left eye target acquisition rate and a right eye target acquisition rate.

6. The method of claim 1, the measuring the first dynamic alignment differential comprising:
measuring the first dynamic alignment differential as a first target acquisition time differential, related to a difference of a left eye target acquisition time and a right eye target acquisition time.

7. The method of claim 6, the measuring comprising:
determining a left eye optical axis angle and a right eye optical axis angle before, or around, the first target shift time;
measuring the left eye target acquisition time as the time representing the left eye optical axis angle acquiring the first-shifted target;
measuring the right eye target acquisition time as the time representing the right eye optical axis angle acquiring the first-shifted target; and
determining a first target acquisition time differential as a difference of the right eye target acquisition time and the left eye target acquisition time.

8. The method of claim 1, the measuring the first dynamic alignment differential comprising:
determining a left eye optical axis angle and a right eye optical axis angle before, or around, the first target shift time;
measuring a left eye target overshoot related to a maximum angle with which the left eye optical axis angle overshoots the first-shifted target;
measuring a right eye target overshoot related to a maximum angle with which the right eye optical axis angle overshoots the first-shifted target; and
determining a first target overshoot differential as a difference of the right eye target overshoot and the left eye target overshoot.

9. The method of claim 1, the measuring the first dynamic alignment differential comprising:
measuring a functional characteristic of the left eye and the right eye tracking the target, wherein the functional characteristic is constructed from at least one of:
a jitter, a lag, a curvature, an S-shape curvature, and a higher derivative.

10. The method of claim 1, wherein:
the determining an average dynamic alignment differential from the first dynamic alignment differential and the second alignment differential includes assigning different weights to the first dynamic alignment differential than to the second alignment differential.

11. The method of claim 1, wherein:

the eye tracker is at least one of an infrared imaging eye tracker, a visible video imaging eye tracker, and a Purkinje-reflection-based eye tracker.

12. The method of claim 1, wherein:

one of the first-shifted target and the second-shifted target is more central than the other target.

13. The method of claim 1, wherein:

one of the first-shifted target and the second-shifted target differs from the starting target in a characteristic other than the target shift angle, including a light intensity, a size, a color, and a shape.

14. The method of claim 1, comprising:

selecting a light intensity of the target to impact a pupil size and thereby a depth of focus of the left and right eyes;

measuring the pupil sizes, optionally with a pupil size tracker;

recording the measured pupil sizes along with the average dynamic alignment differential; and optionally repeating the preceding steps with a different light intensity.

15. The method of claim 1, wherein:

the shifting of the target in the first direction by a first target shift angle is performed in one of a step-like manner, in a non-step-like manner, in a gradual manner, and in a scanning manner.

16. The method of claim 1, wherein:

the shifting of the target in the first direction by a first target shift angle is performed by at the first target shift time presenting a target at the first target shift angle, and simultaneously gradually decreasing a light intensity of the starting target.

17. The method of claim 1, comprising:

performing the method for the target being positioned in an upper hemisphere of a viewing field of the patient to identify an upper average dynamic alignment differential;

performing the method for the target being positioned in a lower hemisphere of the viewing field of the patient to identify a lower average dynamic alignment differential; and determining an upper prescription prism and a lower prescription prism.

18. The method of claim 1, comprising:

determining a prescription prism to reduce the average dynamic alignment differential.

19. The method of claim 18, wherein:

the prescription prism is one of a global prism, a progressive prism, and a contour prism.

20. The method of claim 1, wherein:

the display has two displays with adjustable viewing distances or fixed viewing distances.

21. The method of claim 1, wherein:

the display is single display using at least one of an active shutter technology, a polarized light technology, an image splitting glass technology, and a headset technology.

\* \* \* \* \*